US010213459B2

United States Patent
Yivgi-Ohana et al.

(10) Patent No.: US 10,213,459 B2
(45) Date of Patent: Feb. 26, 2019

(54) COMPOSITIONS OF FUNCTIONAL MITOCHONDRIA AND USES THEREOF

(71) Applicant: Minovia Therapeutics Ltd., Rehovot (IL)

(72) Inventors: Natalie Yivgi-Ohana, Haifa (IL); Uriel Halavee, Ramat Gan (IL)

(73) Assignee: MINOVIA THERAPEUTICS LTD., Rehovot (IL)

( * ) Notice: Subject to any disclaimer, the term of this patent is extended or adjusted under 35 U.S.C. 154(b) by 154 days.

(21) Appl. No.: 14/204,771

(22) Filed: Mar. 11, 2014

(65) Prior Publication Data

US 2014/0193511 A1    Jul. 10, 2014

Related U.S. Application Data

(63) Continuation of application No. PCT/IL2012/050359, filed on Sep. 11, 2012.

(60) Provisional application No. 61/533,233, filed on Sep. 11, 2011.

(51) Int. Cl.
| | | |
|---|---|---|
| A61K 35/00 | (2006.01) | |
| A61K 35/12 | (2015.01) | |
| A61K 35/14 | (2015.01) | |
| A61K 35/50 | (2015.01) | |
| C12N 5/073 | (2010.01) | |
| A61K 47/26 | (2006.01) | |
| A61K 48/00 | (2006.01) | |

(52) U.S. Cl.
CPC .............. *A61K 35/12* (2013.01); *A61K 35/14* (2013.01); *A61K 35/50* (2013.01); *C12N 5/0605* (2013.01); *A61K 47/26* (2013.01); *A61K 48/00* (2013.01)

(58) Field of Classification Search
None
See application file for complete search history.

(56) References Cited

U.S. PATENT DOCUMENTS

| | | | |
|---|---|---|---|
| 7,279,326 B2 | 10/2007 | Weissig et al. | |
| 7,407,800 B1 | 8/2008 | Benton et al. | |
| 2005/0153381 A1* | 7/2005 | Marusich | C07K 16/40 435/7.92 |
| 2010/0278790 A1 | 11/2010 | Prockop et al. | |
| 2011/0008310 A1 | 1/2011 | Cataldo et al. | |
| 2011/0105359 A1 | 5/2011 | Czerwinski | |
| 2012/0058091 A1 | 3/2012 | Rogers et al. | |

FOREIGN PATENT DOCUMENTS

| | | |
|---|---|---|
| WO | 2004100773 A2 | 11/2004 |
| WO | 2008137035 A1 | 11/2008 |
| WO | 2008152640 A2 | 12/2008 |
| WO | 2013/002880 A1 | 1/2013 |
| WO | 2013/171752 A1 | 11/2013 |

OTHER PUBLICATIONS

Pipino et al. British Medical Bulletin 2012; 1-25.*
Griffiths et al. Biochimica et Biophysica Acta 1787 (2009) 1324-1333.*
Kuznetsov et al. Analytical Biochemistry 319, 2003, pp. 296-303.*
Abramova et al., (1979) Injection of mitochondria into oocytes and fertilized eggs. Ontogenez 10(4): 401-5 (Translated abstract).
Abramova et al., (1983) Regulation of the number and function of mitochondria during artificial increase of their mass in fish embryos. Biokhimiia 48(8): 1279-86 (Translated abstract).
Abramova et al., (1989) The functioning of mammalian mitochondria injected into fish embryos. Ontogenez 20(3): 320-3 (Translated abstract).
Bourgeron et al., (1992) Isolation and characterization of mitochondria from human B lymphoblastoid cell lines. Biochem Biophys Res Commun 186(1): 16-23.
Choi et al., (2005) Analysis of proteome bound to D-loop region of mitochondrial DNA by DNA-linked affinity chromatography and reverse-phase liquid chromatography/tandem mass spectrometry. Ann N Y Acad Sci 1042: 88-100.
Clark and Shay (1982) Mitochondrial transformation of mammalian cells. Nature 295(5850): 605-7.
Csordás (2006) Mitochondrial transfer between eukaryotic animal cells and its physiologic role. Rejuvenation Res 9(4): 450-4.
Frazier et al., (2006) Mitochondrial morphology and distribution in mammalian cells. Biol Chem 387(12): 1551-8.
Frezza et al., (2007) Organelle isolation: functional mitochondria from mouse liver, muscle and cultured fibroblasts. Nat Protoc 2(2): 287-95.
Hartwig et al., (2009) A critical comparison between two classical and a kit-based method for mitochondria isolation. Proteomics 9(11): 3209-14.
Katrangi et al., (2007) Xenogenic transfer of isolated murine mitochondria into human rho0 cells can improve respiratory function. Rejuvenation Res 10(4): 561-70.
King and Attardi (1988) Injection of mitochondria into human cells leads to a rapid replacement of the endogenous mitochondrial DNA. Cell 52(6): 811-9.
Martinez et al., (1997) Structural and functional changes in mitochondria associated with trophoblast differentiation: methods to isolate enriched preparations of syncytiotrophoblast mitochondria. Endocrinology 138(5): 2172-83.
McCully et al., (2009) Injection of isolated mitochondria during early reperfusion for cardioprotection. Am J Physiol Heart Circ Physiol 296(1): H94-H105.
Modica-Napolitano and Singh (2002) Mitochondria as targets for detection and treatment of cancer. Expert Rev Mol Med 4(9): 1-19.

(Continued)

*Primary Examiner* — Julie Wu
*Assistant Examiner* — Douglas F White
(74) *Attorney, Agent, or Firm* — Vorys, Sater, Seymour and Pease LLP

(57) ABSTRACT

Mitochondrial compositions and therapeutic methods of using same. Compositions of partially purified functional mitochondria and methods of using the compositions to treat conditions which benefit from increased mitochondrial function by administering the compositions to a subject in need thereof.

9 Claims, 13 Drawing Sheets

(56) References Cited

OTHER PUBLICATIONS

Parone et al., (2008) Preventing mitochondrial fission impairs mitochondrial function and leads to loss of mitochondrial DNA. PLoS One 3(9): e3257.
Pinkert et al., (1997) Mitochondria transfer into mouse ova by microinjection. Transgenic Res 6(6): 379-83.
Plotnikov et al., (2010) Cytoplasm and organelle transfer between mesenchymal multipotent stromal cells and renal tubular cells in co-culture. Exp Cell Res 316(15): 2447-55.
Rousou et al., (2004) Opening of mitochondrial KATP channels enhances cardioprotection through the modulation of mitochondrial matrix volume, calcium accumulation, and respiration. Am J Physiol Heart Circ Physiol 287(5): H1967-76.
Shi et al., (2008) Liposome-mediated transfer of labeled mitochondria into cultured cells. Ethnicity and Disease 18(S1):43-44.
Spees et al., (2006) Mitochondrial transfer between cells can rescue aerobic respiration. Proc Natl Acad Sci U S A 103(5):1283-8.
Szewczyk and Wojtczak (2002) Mitochondria as a pharmacological target. Pharmacol Rev 54(1): 101-27.
Takeda et al., (2005) Microinjection of cytoplasm or mitochondria derived from somatic cells affects parthenogenetic development of murine oocytes. Biol Reprod 72(6): 1397-404.
Tuckey (2005) Progesterone synthesis by the human placenta. Placenta 26(4): 273-81.
Tuckey and Sadleir (1999) The concentration of adrenodoxin reductase limits cytochrome p450scc activity in the human placenta. Eur J Biochem 263(2): 319-25.
Van Blerkom et al., (1998) Mitochondrial transfer between oocytes: potential applications of mitochondrial donation and the issue of heteroplasmy. Hum Reprod 13 (10): 2857-2868.
Wagle et al., (2011) The utility of an isolated mitochondrial fraction in the preparation of liposomes for the specific delivery of bioactives to mitochondria in live mammalian cells. Pharm Res 28(11): 2790-6.
Yamaguchi et al., (2007) Mitochondria frozen with trehalose retain a number of biological functions and preserve outer membrane integrity. Cell Death Differ 14(3): 616-24.
Yasuda et al., (2011) Tunneling nanotubes mediate rescue of prematurely senescent endothelial cells by endothelial progenitors: exchange of lysosomal pool. Aging (Albany NY) 3(6): 597-608.
Gasnier et al., (1993), "Use of Percoll Gradients for Isolation of Human Placenta Mitochondria Suitable for Investigating Outer Membrane Proteins", Anal Biochem, vol. 212, No. 1, pp. 173-178.
Gavazza et al., (2005), "Sensitivity of mitochondria isolated from liver and kidney of rat and bovine to lipid peroxidation: A comparative study of light emission and fatty acid profiles", Mol Cell Biochem, vol. 280, No. 1-2, pp. 77-82.

* cited by examiner

COMPOSITIONS OF FUNCTIONAL MITOCHONDRIA AND USES THEREOF

FIELD OF THE INVENTION

The present invention relates to mitochondrial compositions and therapeutic methods of using same. The invention discloses compositions of partially purified functional mitochondria and methods of using the compositions to treat conditions which benefit from increased mitochondrial function by administering the compositions to a subject in need thereof.

BACKGROUND OF THE INVENTION

Mitochondria are found in nearly all eukaryotic cells and vary in number and location depending on the cell type. Mitochondria contain their own DNA (mtDNA) and their own machinery for synthesizing RNA and proteins. The mtDNA contains only 37 genes, thus most of the gene products in the mammalian body are encoded by nuclear DNA.

Mitochondria perform numerous essential tasks in the eukaryotic cell such as pyruvate oxidation, the Krebs cycle and metabolism of amino acids, fatty acids and steroids. The primary function of mitochondria is the generation of energy as adenosine triphosphate (ATP) by means of the electron-transport chain and the oxidative-phosphorylation system (the "respiratory chain"). Additional processes in which mitochondria are involved include heat production, storage of calcium ions, calcium signaling, programmed cell death (apoptosis) and cellular proliferation. It has been disclosed that mitochondria have a role in cell regulatory and signaling events (i.e. regulation of $Ca^{2+}$ fluxes, oxidative stress and energy-related signaling among others). Therefore, there are many diseases and disorders known in the art associated with malfunction or dysfunction of mitochondria which require efficient treatment.

U.S. Pat. No. 7,279,326 discloses a composition for delivering a wild-type mitochondrial DNA genome to a mammalian cell, the composition comprising: a wild-type mammalian mitochondrial DNA genome molecule; a mitochondrial leader sequence peptide attached to the mitochondrial DNA genome molecule; and a carrier vehicle comprising two delocalized cationic centers separated by a hydrocarbon chain.

Attempts to induce transfer of mitochondria into host cells or tissues have been reported. Most methods require active transfer of the mitochondria by injection (e.g. McCully et al. Am J Physiol Heart Circ Physiol. 2009, 296(1):H94-H105; Van Blerkom et al. Hum Reprod. 1998, 13(10):2857-68; Pinkert et al. Transgenic Res. 1997, 6(6):379-83; King et al. Cell 1988, 25; 52(6):811-9; Abramova et al. Biokhimiia. 1983 August; 48(8):1279-86 and Abramova et al. Ontogenez. 1979; 10(4):401-5). Transfer of mitochondria engulfed within a vehicle, such as a liposome, is also known (e.g. Shi et al. Ethnicity and Disease, 2008; 18(S1):43).

It has been shown that mitochondrial transfer may occur spontaneously between cells in vitro although it was only established that mtDNA was transferred rather than intact whole functional mitochondria (e.g. Plotnikov et al. Exp Cell Res. 2010, 316(15):2447-55; Spees et al. Proc Natl Acad Sci, 2006; 103(5):1283-8). Mitochondrial transfer in-vitro by endocytosis or internalization has been demonstrated as well (Clark et al., Nature, 1982; 295:605-607; Katrangi et al., Rejuvenation Research, 2007; 10(4):561-570).

U.S. 2010/0278790 discloses rescue of ischemic cardiac cells by transfer of mesenchymal stem cells. Without limiting the invention to a particular mechanism, since loss of functional mitochondria is an early consequence of ischemia, MSCs may in part rescue ischemic injury to myocardium or other tissues by transfer of mitochondria or mtDNA.

U.S. 2011/0008310 discloses methods, kits and compositions for mitochondrial replacement in the treatment of disorders arising from mitochondrial dysfunction. This disclosure provides isolated and substantially pure mitochondria for implantation into cells. U.S. 2012/0058091 discloses, inter-alia, an oocyte, an embryonic cell and a modified stem-cell comprising heterologous mitochondria. The mitochondria are delivered in some instances by microinjection in vitro.

Attempts have also been made to use mitochondria that underwent cryopreservation. It has been shown that mitochondria that have been frozen in a buffer comprising trehalose retain a number of biological functions and preserve outer membrane integrity, while showing significantly decreased rates of both phosphorylating and maximally uncoupled respiration (Yamaguchi et al., Cell Death and Differentiation, 2007, (14):616-624). U.S. 2011/0105359 provides cryopreserved compositions of cells in the form of self-sustaining bodies, as well as cellular and subcellular fractions. On the other end, an attempt to inject isolated mitochondria during early reperfusion for cardioprotection showed that cardioprotection requires freshly isolated mitochondria, as frozen mitochondria failed to provide cardioprotection and displayed a significantly decreased oxygen consumption compared with freshly isolated mitochondria (McCully et al., Am. J. Physiol. Heart Circ. Physiol., 2009, (296): H94-H105). Thus, the oxygen consumption rate and functionality of frozen mitochondria is still under debate.

However, there remains an unmet need for an effective and reproducible therapeutic treatment of diseases and disorders associated with nonfunctional or dysfunctional mitochondria.

SUMMARY OF THE INVENTION

The present invention discloses compositions of partially purified functional mitochondria and methods of using the compositions for treatment of conditions which benefit from increased mitochondrial function The present invention is based in part on the unexpected discovery that mitochondria derived from mammalian cells are capable of entering mammalian cells of the same or different origin, while maintaining their functionality within the host cell.

The methods of the invention are useful for the treatment of conditions which benefit from increased mitochondrial function, by introducing partially purified functional mitochondria into a cell or a tissue.

According to one aspect, the invention provides a pharmaceutical composition comprising a plurality of partially purified functional mitochondria, the functional mitochondria having an intact outer membrane; wherein the total amount of mitochondrial proteins does not exceed 80% of the total amount of cellular proteins within the composition; and wherein the composition is devoid of exogenous protease inhibitors.

According to another aspect, the invention provides a method of treating a condition which benefits from increased mitochondrial function, said method comprising:

providing a pharmaceutical composition comprising a plurality of partially purified functional mitochondria, the functional mitochondria having an intact outer membrane; wherein the total amount of mitochondrial proteins does not exceed 80% of the total amount of cellular proteins within the composition; and wherein the composition is devoid of exogenous protease inhibitors; and administering to a subject in need thereof a therapeutically effective amount of the pharmaceutical composition.

According to some embodiments, administration of the composition of the invention to cells results in an increased mitochondrial function of the cells. Increased mitochondrial function may be, but is not limited to, increase in oxygen consumption, ATP production, progesterone production or a combination thereof. Each possibility represents a separate embodiment of the present invention.

According to one embodiment, the partially purified functional mitochondria are derived from a cell or a tissue selected from the group consisting of: placenta, placental cells grown in culture and blood cells.

According to another embodiment, the partially purified functional mitochondria are derived from a cell or a tissue selected from the group consisting of: human placenta, human placental cells grown in culture and human blood cells.

According to some embodiments, the partially purified functional mitochondria are derived from placenta or placental cells grown in culture and the partially purified functional mitochondria produce progesterone or pregnenolone. According to some embodiments, the production of progesterone or pregnenolone is not impaired following a freeze-thaw cycle.

According to some embodiments, the pharmaceutical composition further comprising a buffer, the buffer being the same type of buffer as an isolation buffer used to isolate the partially purified functional mitochondria. According to some embodiments, the isolation buffer is devoid of exogenous protease inhibitors.

According to another embodiment, the pharmaceutical composition further comprises a saccharide in an amount sufficient to preserve mitochondrial function, the saccharide being the same type of saccharide as that used in an isolation buffer to isolate the partially purified functional mitochondria. According to some embodiments, the saccharide is sucrose. According to some embodiments the saccharide is other than trehalose.

According to another embodiment, the composition of the invention does not comprise mitochondrial clumps or cellular components larger than 5 μm. According to some embodiments, the composition of the invention is filtered through a 5 μm filter to remove any intact cells, cell debris or aggregates. Use of compositions comprising mitochondrial aggregates according to the methods of the invention may be less efficient and even detrimental to the subject.

According to some embodiments, the mitochondria of the invention are exposed to an ion-exchanger inhibitor. According to some embodiments, the mitochondria of the invention are reduced in size by exposure to an ion-exchanger inhibitor. According to some embodiments, the ion-exchanger inhibitor is CGP37157. According to another embodiment, the final pharmaceutical composition is devoid of free ion-exchanger inhibitor.

According to another embodiment, the partially purified functional mitochondria have undergone a freeze-thaw cycle. According to another embodiment, the freeze-thaw cycle comprises freezing the partially purified functional mitochondria within a freezing buffer, the freezing buffer comprising a cryoprotectant. According to some embodiments the cryoprotectant is a saccharide.

According to some embodiments, the freeze-thaw cycle comprises freezing said partially purified functional mitochondria for at least 24 hours prior to thawing. According to some embodiments, the freeze-thaw cycle comprises freezing said partially purified functional mitochondria for at least 1 month prior to thawing, several months prior to thawing or longer. According to another embodiment, the oxygen consumption of the partially purified functional mitochondria after the freeze-thaw cycle is equal or higher than the oxygen consumption of the partially purified functional mitochondria prior to the freeze-thaw cycle.

According to some embodiments, the conditions which benefit from increased mitochondrial function are diseases and disorders associated with nonfunctional or dysfunctional mitochondria. Each possibility represents a separate embodiment of the present invention. According to another embodiment, the disease or disorder associated with non-functional or dysfunctional mitochondria is selected from the group consisting of: a mitochondrial disease caused by damage to mtDNA, a mitochondrial disease caused by damage to nuclear genes and a mitochondrial disease caused by a toxin. According to another embodiment, the damage is selected from the group consisting of: mutation, deletion, truncation, cross-linking and a combination thereof.

According to another embodiment, administering to a subject is by a route selected from the group consisting of: intravenous, intraarterial, intramuscular, intralesional, transmucosal, subcutaneous, through inhalation and via direct injection into a tissue or an organ.

According to some embodiments administering mitochondria to a subject is performed ex-vivo, either to cells of the subject or of a donor and the cells are then administered to the subject.

According to another embodiment, the partially purified functional mitochondria are from a source selected from autologous, allogeneic and xenogeneic. According to some embodiments, the partially purified functional mitochondria are derived from a donor.

According to another aspect, the present invention provides a composition for pro-apoptotic protein delivery comprising a plurality of modified mitochondria comprising an intact mitochondrial outer membrane, the mitochondria harboring at least one exogenous pro-apoptotic protein.

According to yet another aspect, the present invention provides a method of delivering a pro-apoptotic protein to a cell comprising:

providing a pharmaceutical composition comprising a plurality of modified mitochondria comprising an intact mitochondrial outer membrane, the mitochondria harboring at least one exogenous pro-apoptotic protein; and administering the composition comprising modified mitochondria to a cell.

According to yet another aspect, the present invention provides a method of delivering a pro-apoptotic protein to a subject comprising:

providing a pharmaceutical composition comprising a plurality of modified mitochondria comprising an intact mitochondrial outer membrane, the mitochondria harboring at least one exogenous pro-apoptotic protein; and administering the composition comprising modified mitochondria to a subject in need thereof.

According to another embodiment, the pro-apoptotic protein is a member of the Bcl-2 family. According to another embodiment, the member of the Bcl-2 family is selected from the group consisting of: Bid, Bax, Puma, Bim, Bmf, Bad, Bcl-$X_S$, Erk, Bok and Bik. According to another embodiment, the pro-apoptotic protein is selected from the group consisting of: cytochrome c, apoptosis-inducing factor, a caspase and a procaspase.

According to another embodiment, the modified mitochondria are isolated from cells expressing the exogenous pro-apoptotic protein.

According to another embodiment, the pro-apoptotic protein is bound to a mitochondrial membrane of the modified mitochondria. According to another embodiment, the pro-apoptotic protein is within the intermembrane space of the modified mitochondria. According to another embodiment, the pro-apoptotic protein is diffused within the matrix of the modified mitochondria.

According to another embodiment, the modified mitochondria are further conjugated to a cell targeting molecule enabling targeted pro-apoptotic protein delivery. According to another embodiment, the cell targeting molecule is selected from the group consisting of: an antibody, an oligosaccharide, a peptide and a carbohydrate. Further embodiments, features, advantages and the full scope of applicability of the present invention will become apparent from the detailed description and drawings given hereinafter. However, it should be understood that the detailed description, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1A:
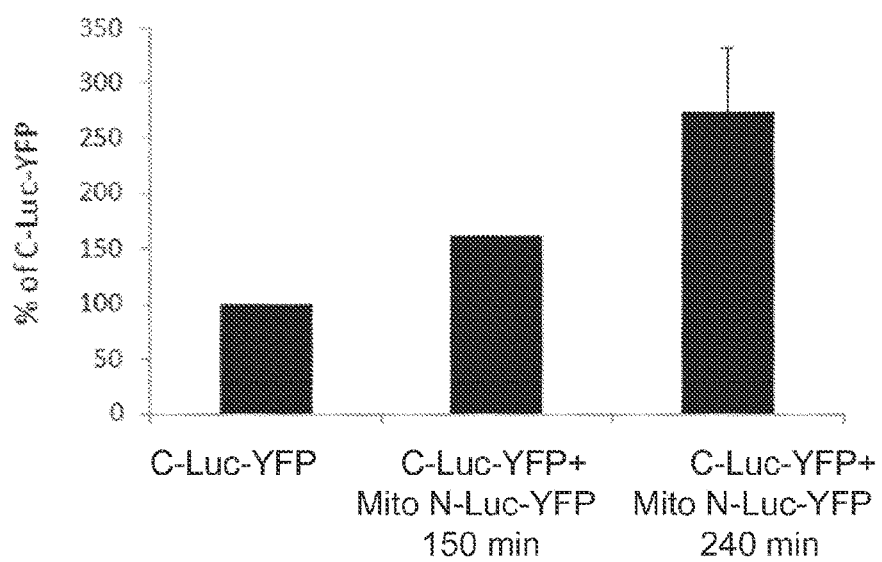
FIG. 1A is a bar graph showing luciferase complementation in 3T3-L1 fibroblast cells expressing C-Luc-YFP with or without incubation with mitochondria extracted from cells expressing N-Luc-YFP.

The present invention relates to mitochondria compositions comprising partially purified functional mitochondria and methods of using same for treating conditions which benefit from increased mitochondrial function.

According to one aspect, the present invention provides a pharmaceutical composition comprising a plurality of partially purified functional mitochondria, the functional mitochondria having an intact outer membrane; wherein the total amount of mitochondrial proteins do not exceed 80% of the total amount of cellular proteins within the composition; and wherein the composition is devoid of exogenous protease inhibitors.

According to another aspect, the present invention provides a method of treating conditions which benefit from increased mitochondrial function, the method comprising:

providing a pharmaceutical composition comprising a plurality of partially purified functional mitochondria, the functional mitochondria having an intact outer membrane; wherein the total amount of mitochondrial proteins do not exceed 80% of the total amount of cellular proteins within the composition; and wherein the composition is devoid of exogenous protease inhibitors; and administering to a subject in need thereof a therapeutically effective amount of the pharmaceutical composition.

Mitochondria include the mitochondrial genome which is a circular double-stranded molecule, consisting of 16,569 base pairs. It contains 37 genes including 13 protein-encoding genes, 22 transfer RNA (tRNA) genes and two ribosomal RNA (rRNA) genes. The 13 protein-encoding genes are components of the mitochondrial respiratory chain. The wild type (wt)-mtDNA molecule may also include sequence polymorphism, but it remains fully functional. Structurally, mitochondria organelles range in diameter or width from 0.5 μm to 1 μm and have four compartments: the outer membrane, the inner membrane, the intermembrane space and the matrix.

According to some embodiments, the term "functional mitochondria" refers to mitochondria that consume oxygen. According to another embodiment, functional mitochondria have an intact outer membrane. According to some embodiments, functional mitochondria are intact mitochondria. In another embodiment, functional mitochondria consume oxygen at an increasing rate over time. In another embodiment, the functionality of mitochondria is measured by oxygen consumption. In another embodiment, oxygen consumption of mitochondria may be measured by any method known in the art such as, but not limited to, the MitoXpress fluorescence probe (Luxcel). According to some embodiments, functional mitochondria are mitochondria which display an increase in the rate of oxygen consumption in the presence of ADP and a substrate such as, but not limited to, glutamate, malate or succinate. Each possibility represents a separate embodiment of the present invention. In another embodiment, functional mitochondria are mitochondria which produce ATP. In another embodiment, functional mitochondria are mitochondria capable of manufacturing their own RNAs and proteins and are self-reproducing structures. In another embodiment, functional mitochondria produce a mitochondrial ribosome and mitochondrial tRNA molecules.

As is known in the art, functional placental mitochondria participate in production of progesterone (see, for example, Tuckey R C, Placenta, 2005, 26(4):273-81). According to some embodiments, functional mitochondria are mitochondria which produce progesterone or pregnenolone. Each possibility represents a separate embodiment of the present invention. According to some embodiments, functional mitochondria are mitochondria which secrete progesterone. In a non-limiting example, partially purified functional mitochondria derived from placenta or placental cells grown in culture produce progesterone or pregnenolone. Each possibility represents a separate embodiment of the present invention. According to some embodiments, the partially purified functional mitochondria of the invention are derived from placenta or placental cells grown in culture and the partially purified functional mitochondria produce progesterone or pregnenolone. Each possibility represents a separate embodiment of the present invention. According to some embodiments, the production of progesterone or pregnenolone in the partially purified functional mitochondria of the invention is not impaired following a freeze-thaw cycle. According to some embodiments, the functionality of mitochondria is measured by measuring mitochondrial progesterone production or mitochondrial production of progesterone precursors such as, but not limited to, pregnenolone. Each possibility represents a separate embodiment of the present invention. Progesterone production may be measured by any assay known in the art such as, but not limited to, a radioimmunoassay (RIA). According to some embodiments, administration of mitochondria which secrete progesterone results in progesterone production in the host cell. According to other embodiments, administration of mitochondria which secrete progesterone to host cells which do not otherwise produce progesterone results in progesterone production in the host cells.

As used herein, the term "intact mitochondria" refers to mitochondria comprising an outer and an inner membrane, an inter-membrane space, the cristae (formed by the inner membrane) and the matrix. In another embodiment, intact mitochondria comprise mitochondrial DNA. In another embodiment, intact mitochondria contain active respiratory chain complexes I-V embedded in the inner membrane. In another embodiment, intact mitochondria consume oxygen. As used herein, the term "mitoplasts" refers to mitochondria devoid of outer membrane.

According to another embodiment, intactness of a mitochondrial membrane may be determined by any method known in the art. In a non-limiting example, intactness of a mitochondrial membrane is measured using the tetramethylrhodamine methyl ester (TMRM) or the tetramethylrhodamine ethyl ester (TMRE) fluorescent probes. Each possibility represents a separate embodiment of the present invention. Mitochondria that were observed under a microscope and show TMRM or TMRE staining have an intact mitochondrial outer membrane.

As used herein, the term "a mitochondrial membrane" refers to a mitochondrial membrane selected from the group consisting of: the mitochondrial inner membrane, the mitochondrial outer membrane or a combination thereof.

As used herein, the term "partially purified mitochondria" refers to mitochondria separated from other cellular components, wherein the weight of the mitochondria constitutes between 20-80%, preferably 30-80%, most preferably 40-70% of the combined weight of the mitochondria and other sub-cellular fractions (as exemplified in: Hartwig et al., Proteomics, 2009, (9):3209-3214). Each possibility represents a separate embodiment of the present invention.

According to another embodiment, partially purified mitochondria do not contain intact cells. According to another embodiment, the composition of the invention does not comprise intact cells. According to another embodiment, the composition of the invention does not comprise mitochondrial clumps or aggregates or cellular debris or components larger than 5 µm. Each possibility represents a separate embodiment of the present invention. According to another embodiment, the composition of the invention is devoid of particulate matter greater than 5 µm. As used herein, the term "particulate matter" refers to intact cells, cell debris, aggregates of mitochondria, aggregates of cellular debris or a combination thereof. Each possibility represents a separate embodiment of the present invention. As used herein, a composition devoid of exogenous particulate matter greater than 5 µm comprises no more than 1 µM of particulate matter greater than 5 µm, preferably less than 0.5 µM, most preferably less than 0.1 µM.

According to some embodiments, intact cells, cell debris or aggregates are removed from the composition of the invention. According to some embodiments, the composition of the invention is filtered through a filter of no more than 5 µm, in order to remove any intact cells, cell debris or aggregates, as exemplified herein below. Without wishing to be bound by any theory or mechanism, use of compositions comprising mitochondrial clumps according to the methods of the invention may be less efficient and even detrimental to the subject. According to another embodiment, the composition of the invention does not comprise liposomes or any other particulate carrier. Each possibility represents a separate embodiment of the present invention.

According to another embodiment, the weight of the mitochondria in partially purified mitochondria constitutes at least 20% of the combined weight of the mitochondria and other sub-cellular fractions. According to another embodiment, the weight of the mitochondria in partially purified mitochondria constitutes between 20%-40% of the combined weight of the mitochondria and other sub-cellular fractions. According to another embodiment, the weight of the mitochondria in partially purified mitochondria constitutes between 40%-80% of the combined weight of the mitochondria and other sub-cellular fractions. According to another embodiment, the weight of the mitochondria in partially purified mitochondria constitutes between 30%-70% of the combined weight of the mitochondria and other sub-cellular fractions. According to another embodiment, the weight of the mitochondria in partially purified mitochondria constitutes between 50%-70% of the combined weight of the mitochondria and other sub-cellular fractions.

According to another embodiment, the weight of the mitochondria in partially purified mitochondria constitutes between 60%-70% of the combined weight of the mitochondria and other sub-cellular fractions. According to another embodiment, the weight of the mitochondria in partially purified mitochondria constitutes less than 80% of the combined weight of the mitochondria and other sub-cellular fractions.

As used herein, the term "isolated mitochondria" refers to mitochondria separated from other cellular components, wherein the weight of the mitochondria constitutes more than 80% of the combined weight of the mitochondria and other sub-cellular fractions. Preparation of isolated mitochondria may require changing buffer composition or additional washing steps, cleaning cycles, centrifugation cycles and sonication cycles which are not required in preparation of partially purified mitochondria. Without wishing to be bound by any theory or mechanism, such additional steps and cycles may harm the functionality of the isolated mitochondria.

According to another embodiment, the weight of the mitochondria in isolated mitochondria constitutes more than 90% of the combined weight of the mitochondria and other sub-cellular fractions. A non-limiting example of a method for obtaining isolated mitochondria is the MACS® technology (Miltenyi Biotec). Without wishing to be bound by any theory or mechanism, isolated mitochondria in which the weight of the mitochondria constitutes more than 95% of the combined weight of the mitochondria and other sub-cellular fractions are not functional mitochondria. According to another embodiment, isolated mitochondria do not contain intact cells.

According to another embodiment, the mitochondria of the invention are partially purified mitochondria. According to another embodiment, the mitochondria of the invention are functional mitochondria. According to another embodiment, the mitochondria of the invention are functional partially purified mitochondria. According to some embodiments, the mitochondria of the invention are modified mitochondria. According to other embodiments, the mitochondria of the invention are partially purified modified mitochondria. According to some embodiments, the mitochondria of the invention are isolated modified mitochondria.

According to another embodiment, the total amount of mitochondrial proteins in the composition of the invention does not exceed 80% of the total amount of cellular proteins within the composition. According to another embodiment, the total amount of mitochondrial proteins in the composition of the invention does not exceed 80%, 70%, 60%, 50%, 40%, 30%, 20% of the total amount of cellular proteins within the composition. Each possibility represents a separate embodiment of the present invention. According to some embodiments, the total amount of mitochondrial proteins in the composition of the invention is between 70%-80% of the total amount of cellular proteins within the composition. According to some embodiments, the total amount of mitochondrial proteins in the composition of the invention is between 60%-80% of the total amount of cellular proteins within the composition. According to some embodiments, the total amount of mitochondrial proteins in the composition of the invention is between 60%-70% of the total amount of cellular proteins within the composition. According to some embodiments, the total amount of mitochondrial proteins in the composition of the invention is between 60%-80% of the total amount of cellular proteins within the composition. According to some embodiments, the total amount of mitochondrial proteins in the composition of the invention is between 20%-80% of the total amount of cellular proteins within the composition. According to some embodiments, the total amount of mitochondrial proteins in the composition of the invention is between 20%-50% of the total amount of cellular proteins within the composition.

As used herein, the term "mitochondrial proteins" refers to proteins which originate from mitochondria, including mitochondrial proteins which are encoded by genomic DNA or mtDNA. As used herein, the term "cellular proteins" refers to all proteins which originate from the cells or tissue from which the mitochondria are produced.

According to another embodiment, the composition of the invention is devoid of exogenous protease inhibitors. As used herein, the term "exogenous protease inhibitors" refers to protease inhibitors which do not originate from the cells or tissue from which the mitochondria of the invention are extracted. According to another embodiment, exogenous protease inhibitors are protease inhibitors which are added to the composition of the invention prior to or following extraction of the mitochondria of the invention. Each possibility represents a separate embodiment of the present invention.

According to another embodiment, the mitochondria isolation buffer is devoid of exogenous protease inhibitors. Protease inhibitors, as used herein, are any protease inhibitors known in the art, including, but not limited to, aprotinin, bestatin, E-64, leupeptin and pepstatin A.

As used herein, a composition devoid of exogenous protease inhibitors comprises no more than 1 µM of exogenous protease inhibitors, preferably less than 0.5 µM, most preferably less than 0.1 µM. It is to be noted that the composition of the invention may comprise endogenous protease inhibitors originating from the cells or tissue from which the mitochondria of the invention are extracted. Without wishing to be bound by any theory or mechanism, addition of exogenous protease inhibitors to the composition of the invention may reduce functionality of the mitochondria (as exemplified herein below in Example 13). According to another embodiment, the mitochondria of the invention have undergone a freeze-thaw cycle. Without wishing to be bound by any theory or mechanism, mitochondria that have undergone a freeze-thaw cycle demonstrate a comparable or higher oxygen consumption rate following thawing, as compared to control mitochondria that have not undergone a freeze-thaw cycle. Thus, mitochondria that have undergone a freeze-thaw cycle are at least as functional as control mitochondria that have not undergone a freeze-thaw cycle.

As used herein, the term "freeze-thaw cycle" refers to freezing of the mitochondria of the invention to a temperature below 0° C., maintaining the mitochondria in a temperature below 0° C. for a defined period of time and thawing the mitochondria to room temperature or body temperature or any temperature above 0° C. which enables administering the mitochondria according to the methods of the invention. Each possibility represents a separate embodiment of the present invention. The term "room temperature", as used herein refers to a temperature of between 18° C. and 25° C. The term "body temperature", as used herein, refers to a temperature of between 35.5° C. and 37.5° C., preferably 37° C. In another embodiment, mitochondria that have undergone a freeze-thaw cycle are functional mitochondria.

In another embodiment, the mitochondria that have undergone a freeze-thaw cycle were frozen at a temperature of at least −70° C. In another embodiment, the mitochondria that have undergone a freeze-thaw cycle were frozen at a temperature of at least −20° C. In another embodiment, the mitochondria that have undergone a freeze-thaw cycle were frozen at a temperature of at least −4° C. In another embodiment, the mitochondria that have undergone a freeze-thaw cycle were frozen at a temperature of at least 0° C. According to another embodiment, freezing of the mitochondria is gradual. According to some embodiment, freezing of mitochondria is through flash-freezing. As used herein, the term "flash-freezing" refers to rapidly freezing the mitochondria by subjecting them to cryogenic temperatures.

In another embodiment, the mitochondria that underwent a freeze-thaw cycle were frozen for at least 30 minutes prior to thawing. According to another embodiment, the freeze-thaw cycle comprises freezing the partially purified functional mitochondria for at least 30, 60, 90, 120, 180, 210 minutes prior to thawing. Each possibility represents a separate embodiment of the present invention. In another embodiment, the mitochondria that have undergone a freeze-thaw cycle were frozen for at least 1,2,3,4,5,6,7,8,9, 10,24,48,72,96,120 hours prior to thawing. Each freezing time presents a separate embodiment of the present invention. In another embodiment, the mitochondria that have undergone a freeze-thaw cycle were frozen for at least 4, 5, 6, 7, 30, 60, 120, 365 days prior to thawing. Each freezing time presents a separate embodiment of the present invention. According to another embodiment, the freeze-thaw cycle comprises freezing the partially purified functional mitochondria for at least 1, 2, 3 weeks prior to thawing. Each possibility represents a separate embodiment of the present invention. According to another embodiment, the freeze-thaw cycle comprises freezing the partially purified functional mitochondria for at least 1, 2, 3, 4, 5, 6 months prior to thawing. Each possibility represents a separate embodiment of the present invention.

In another embodiment, the mitochondria that have undergone a freeze-thaw cycle were frozen at −70° C. for at least 30 minutes prior to thawing. Without wishing to be bound by any theory or mechanism, the possibility to freeze mitochondria and thaw them after a long period (as exemplified herein below in example 10) enables easy storage and use of the mitochondria with reproducible results even after a long period of storage.

According to another embodiment, thawing is at room temperature. In another embodiment, thawing is at body temperature. According to another embodiment, thawing is at a temperature which enables administering the mitochondria according to the methods of the invention. According to another embodiment, thawing is performed gradually.

According to another embodiment, the mitochondria that underwent a freeze-thaw cycle were frozen within a freezing buffer. According to another embodiment, the mitochondria that underwent a freeze-thaw cycle were frozen within the isolation buffer. As used herein, the term "isolation buffer" refers to a buffer in which the mitochondria of the invention have been partially purified. In a non-limiting example, the isolation buffer comprises 200 mM sucrose, 10 mM Tris-MOPS and 1 mM EGTA. According to some embodiments, BSA (Bovine Serum Albumin) is added to the isolation buffer during partial purification. According to some embodiments, 0.2% BSA is added to the isolation buffer during partial purification. According to some embodiments, HSA (Human Serum Albumin) is added to the isolation buffer during partial purification. According to some embodiments, 0.2% HSA is added to the isolation buffer during partial purification. According to other embodiment, HSA or BSA is washed away from the mitochondria of the invention following partial purification. Each possibility represents a separate embodiment of the present invention. Without wishing to be bound by any mechanism or theory, freezing mitochondria within the isolation buffer saves time and isolation steps, as there is no need to replace the isolation buffer with a freezing buffer prior to freezing or to replace the freezing buffer upon thawing.

According to another embodiment, the freezing buffer comprises a cryoprotectant. According to some embodiments, the cryoprotectant is a saccharide, an oligosaccharide or a polysaccharide. Each possibility represents a separate embodiment of the present invention. According to another embodiment, the saccharide concentration in the freezing buffer is a sufficient saccharide concentration which acts to preserve mitochondrial function. According to another embodiment, the isolation buffer comprises a saccharide. According to another embodiment, the saccharide concentration in the isolation buffer is a sufficient saccharide concentration which acts to preserve mitochondrial function. According to another embodiment, the saccharide is sucrose. According to another embodiment, the saccharide is other than trehalose. Without wishing to be bound by any theory or mechanism, mitochondria that have been frozen within a freezing buffer or isolation buffer comprising sucrose demonstrate a comparable or higher oxygen consumption rate following thawing, as compared to control mitochondria that have not undergone a freeze-thaw cycle or that have been frozen within a freezing buffer or isolation buffer without sucrose.

According to another embodiment, the composition of the invention further comprises a saccharide an oligosaccharide or a polysaccharide. Each possibility represents a separate embodiment of the present invention. It is noted that, as referred to herein, saccharide may refer to an oligosaccharide or a polysaccharide. According to another embodiment, the composition of the invention further comprises a carrier. According to some embodiments, the carrier is a cell culture medium. According to another embodiment, the composition of the invention comprises a saccharide in an amount sufficient to preserve mitochondrial function, the saccharide being the same type of saccharide as that used in an isolation buffer to isolate the partially purified functional mitochondria of the invention. According to another embodiment, the composition of the invention comprises a buffer, the buffer being the same type of buffer as an isolation buffer used to isolate the partially purified functional mitochondria of the invention.

As used herein, the terms "composition of the invention", "the composition", and "mitochondria composition of the invention" are used interchangeably.

According to some embodiments, addition of a saccharide to the mitochondria composition of the invention at a sufficient concentration acts to preserve mitochondrial function. According to another embodiment, a sufficient saccharide concentration which acts to preserve mitochondrial function is a concentration of between 100 mM-400 mM, preferably between 100 mM-250 mM, most preferably between 200 mM-250 mM. Each possibility represents a separate embodiment of the present invention. According to another embodiment, the saccharide according to the invention is sucrose. According to some embodiments the saccharide of the invention is other than trehalose. According to some embodiments the saccharide of the invention is other than mannitol.

According to another embodiment, the saccharide concentration in the composition of the invention is between 100 mM-150 mM. According to another embodiment, the saccharide concentration in the composition of the invention is between 150 mM-200 mM. According to another embodiment, the saccharide concentration in the composition of the invention is between 100 mM-200 mM. According to another embodiment, the saccharide concentration in the composition of the invention is between 100 mM-400 mM. According to another embodiment, the saccharide concentration in the composition of the invention is between 150 mM-400 mM. According to another embodiment, the saccharide concentration in the composition of the invention is between 200 mM-400 mM. According to another embodiment, the saccharide concentration in the composition of the invention is at least 100 mM. According to another embodiment, the saccharide concentration in the composition of the invention is at least 200 mM. Without wishing to be bound by any theory or mechanism of action, a saccharide concentration below 100 mM may not be sufficient to preserve mitochondrial function.

According to another embodiment, preserving mitochondrial function according to the invention is preserving mitochondrial ability to consume oxygen. In another embodiment, preserving mitochondrial function according to the invention is preserving mitochondrial ability to consume oxygen at an increasing rate over time. According to another embodiment, preserving mitochondrial function according to the invention is preserving mitochondrial ability to produce progesterone.

According to some embodiments, the mitochondria of the invention are exposed to an ion-exchanger inhibitor. According to some embodiments, the mitochondria of the invention are reduced in size by exposure to an ion-exchanger inhibitor. According to another embodiment, the partially purified functional mitochondria of the invention were reduced in size by exposure to an ion-exchanger inhibitor. According to some embodiments, the mitochondria of the invention are exposed to the ion-exchanger inhibitor following partial purification. According to some embodiments, the mitochondria of the invention are exposed to the ion-exchanger inhibitor during partial purification. According to other embodiments, the cells or tissue from which the mitochondria of the invention are derived are exposed to the ion-exchanger inhibitor prior to partial purification of the mitochondria. Each possibility represents a separate embodiment of the present invention. According to another embodiment, the ion-exchanger inhibitor is CGP37157. As used herein, the terms "CGP" and "CGP37157" are used interchangeably. Without wishing to be bound by any theory or mechanism, agents blocking the mitochondrial $Na^+/Ca^{2+}$ exchanger, such as, CGP37157 may induce mitochondrial fission, increase mitochondrial ATP production and reduce mitochondrial size. Reduced mitochondrial size may facilitate mitochondrial entry to cells.

According to another embodiment, the final pharmaceutical composition is devoid of free ion-exchanger inhibitor. As used herein, a composition devoid of ion-exchanger inhibitor refers to a composition devoid of ion-exchanger inhibitor which is not bound to the mitochondria of the invention. According to some embodiments, the composition of the invention comprises an ion-exchanger inhibitor bound to the mitochondria of the invention. According to some embodiments, a composition devoid of ion-exchanger inhibitor comprises an ion-exchanger inhibitor at a concentration of less than 1 µM of, preferably less than 0.5 µM, most preferably less than 0.1 µM.

The mitochondria according to the invention may be obtained by methods disclosed herein or by any other method known in the art. Commercially available mitochondria isolation kits include, for example Mitochondria Isolation Kit, MITOISO1 (Sigma-Aldrich), among others.

According to another embodiment, the partially purified functional mitochondria are derived from the subject in need thereof. According to another embodiment, the partially purified functional mitochondria are derived from a different subject than the subject in need thereof. According to another embodiment, the partially purified functional mitochondria are derived from the same subject to whom they are administered. According to another embodiment, the partially purified functional mitochondria are derived from a different subject than the subject to whom they are administered. According to another embodiment, the partially purified functional mitochondria of the invention are from a source selected from autologous, allogeneic and xenogeneic. Each possibility represents a separate embodiment of the present invention. As used herein, mitochondria of an autologous source refer to mitochondria derived from the same subject to be treated. As used herein, mitochondria of an allogeneic source refer to mitochondria derived from a different subject than the subject to be treated from the same species. As used herein, mitochondria of a xenogeneic source refer to mitochondria derived from a different subject than the subject to be treated from a different species. According to another embodiment, the partially purified functional mitochondria of the invention are derived from a donor. According to some embodiments, the donor is an allogeneic donor. According to some embodiments, the donor is an autologous donor.

According to another embodiment, the mitochondria of the invention are derived from a mammalian subject. According to another embodiment, the mammalian subject is a human subject. According to another embodiment, the mammalian subject is selected from a group consisting of: a human, a horse, a dog, a cat, a mouse, a rat, a cow and a sheep. Each possibility represents a separate embodiment of the present invention. According to another embodiment, the mitochondria of the invention are derived from a mammalian cell. According to another embodiment, the mammalian cell is a human cell. According to another embodiment, the mitochondria are derived from cells in culture. According to another embodiment, the mitochondria are derived from a tissue.

According to another embodiment, the mitochondria of the invention are derived from a cell or a tissue selected from the group consisting of: human placenta, human placental cells grown in culture and human blood cells. According to another embodiment, the mitochondria of the invention are derived from a cell or a tissue selected from the group consisting of: placenta, placental cells grown in culture and blood cells.

The terms "host cell", "acceptor cell" and "recipient cell" are interchangeably used herein to describe a cell receiving and encompassing (harboring) exogenous mitochondria. According to another embodiment, the mitochondria of the invention are exogenous mitochondria. The terms "donor cell" or "donor tissue", as used herein, refer to a cell or a tissue, respectively, from which the mitochondria of the invention are derived.

As used herein. the phrases "cells grown in culture" or "a tissue grown in culture" refers to a multitude of cells or a tissue, respectively, grown in a liquid, semi-solid or solid medium, outside of the organism from which the cells or tissue derive. According to some embodiments, cells grown in culture are cells grown in bioreactors. According to a non-limiting example, cells may be grown in a bioreactor (such as, but not limited to the bioreactor disclosed in WO 2008/152640), followed by isolation of partially purified functional mitochondria from the cells.

According to some embodiments, a condition which benefits from increased mitochondrial function is a disease or disorder associated with nonfunctional or dysfunctional mitochondria. As used herein, "a disease or disorder associated with nonfunctional or dysfunctional mitochondria" is a disease or disorder which is caused by or is aggravated by mitochondria which are not functioning as healthy mitochondria or are not functioning at all or are structurally impaired. Each possibility represents a separate embodiment of the present invention. According to some embodiments, the disease or disorder associated with nonfunctional or dysfunctional mitochondria is selected from the group consisting of: a mitochondrial disease caused by damage to mtDNA, a mitochondrial disease caused by damage to nuclear genes and a mitochondrial disease caused by a toxin. According to certain embodiments, the toxin is selected from the group consisting of: 3-nitropropionic acid, 1-methyl-4-phenyl-1,2,5,6-tetrahydropyridine, annonacin, rotenone and tetrahydroisoquinolines. According to another embodiment, the damage is selected from the group consisting of: mutation, deletion, truncation, cross-linking and a combination thereof.

Non limiting examples of a disease or disorder associated with nonfunctional or dysfunctional mitochondria include Diabetes mellitus and deafness (DAD), Leber's hereditary optic neuropathy (LHON), visual loss beginning in young adulthood, eye disorder characterized by progressive loss of central vision due to degeneration of the optic nerves and retina, Wolff-Parkinson-White syndrome, multiple sclerosis-type disease, Leigh syndrome, subacute sclerosing encephalopathy, neuropathy, ataxia, retinitis pigmentosa, ptosis, dementia, myoneurogenic gastrointestinal encephalopathy (MNGIE), gastrointestinal pseudo-obstruction, myoclonic epilepsy with ragged red fibers (MERRF), short stature, hearing loss, lactic acidosis, mitochondrial myopathy, encephalomyopathy, lactic acidosis, stroke-like symptoms (MELAS) and mitochondrial neurogastrointestinal encephalomyopathy.

According to another embodiment, the partially purified functional mitochondria of the invention comprise at least one protein, or a gene encoding the at least one protein, capable of inhibiting, ameliorating or preventing said disease or disorder associated with nonfunctional or dysfunctional mitochondria. Each possibility represents a separate embodiment of the present invention.

The term "therapeutically effective amount" as used herein refers to the amount of composition of the invention effective to treat or ameliorate a condition which benefits from increased mitochondrial function in a subject in need thereof.

The term "subject in need thereof", as used herein, refers to a subject afflicted with, or at a risk of being afflicted with, a condition which benefits from increased mitochondrial function. Each possibility represents a separate embodiment of the present invention. According to some embodiments, "a subject in need thereof" is a subject afflicted with a condition which may benefit from pro-apoptotic activity. In a non-limiting example, a condition which may benefit from pro-apoptotic activity is cancer. According to another embodiment, a subject in need thereof is mammalian. According to another embodiment, a subject in need thereof is human. According to another embodiment, a subject in need thereof is selected from the group consisting of: a human, a horse, a dog, a cat, a mouse, a rat, a cow and a sheep.

Any suitable route of administration to a subject may be used for the composition of the present invention, including but not limited to topical and systemic routes. According to some embodiments, administering is administering systemically. According to some embodiments, the composition is formulated for systemic administration.

According to another embodiment, administration systemically is through a parenteral route. According to some embodiments, preparations of the composition of the invention for parenteral administration include sterile aqueous or non-aqueous solutions, suspensions, or emulsions, each representing a separate embodiment of the present invention. Non-limiting examples of non-aqueous solvents or vehicles are propylene glycol, polyethylene glycol, vegetable oils such as olive oil and corn oil, gelatin, and injectable organic esters such as ethyl oleate.

According to some embodiments, parenteral administration is administration intravenously, intra-arterially, intramuscularly, intraperitoneally, intradermally, intravitreally, or subcutaneously. Each of the above-mentioned administration routes represents a separate embodiment of the present invention. According to another embodiment, parenteral administration is performed by bolus injection. According to another embodiment, parenteral administration is performed by continuous infusion.

According to another embodiment, parenteral administration is transmucosal administration. According to another embodiment, transmucosal administration is transnasal administration. For transmucosal administration, penetrants appropriate to the barrier to be permeated are used in the formulation. Such penetrants are generally known in the art. The preferred mode of administration will depend upon the particular indication being treated and will be apparent to one of skill in the art.

According to another embodiment, systemic administration of the composition is through injection. For administration through injection, the composition may be formulated in an aqueous solution, for example in a physiologically compatible buffer including but not limited to Hank's solution, Ringer's solution, or physiological salt buffer. Formulations for injection may be presented in unit dosage forms, for example, in ampoules, or in multi-dose containers with, optionally, an added preservative. According to another embodiment, administration is through convection enhanced delivery (CED).

Aqueous injection suspensions may contain substances that increase the viscosity of the suspension, such as sodium carboxymethyl cellulose, sorbitol, or dextran. Optionally, the suspension may also contain suitable stabilizers or agents that increase the solubility of the active ingredients, to allow for the preparation of highly concentrated solutions.

According to another embodiment, compositions formulated for injection may be in the form of solutions, suspensions, dispersions or emulsions in oily or aqueous vehicles, and may contain formulatory agents such as suspending, stabilizing, and/or dispersing agents. Non-limiting examples of suitable lipophilic solvents or vehicles include fatty oils such as sesame oil, or synthetic fatty acid esters such as ethyl oleate or triglycerides.

According to another embodiment, the composition is administered intravenously, and is thus formulated in a form suitable for intravenous administration. According to another embodiment, the composition is administered intra-arterially, and is thus formulated in a form suitable for intra-arterial administration. According to another embodiment, the composition is administered intramuscularly, and is thus formulated in a form suitable for intramuscular administration.

According to another embodiment, parenteral administration is through inhalation. For administration by inhalation route, the active ingredients are conveniently delivered in the form of an aerosol spray presentation from a pressurized pack or a nebulizer with the use of a suitable propellant, for example, dichlorodifluoromethane, trichlorofluoromethane, dichloro-tetrafluoroethane, or carbon dioxide. In the case of a pressurized aerosol, the dosage may be determined by providing a valve to deliver a metered amount. The preferred mode of administration will depend upon the particular indication being treated and will be apparent to one of skill in the art. According to some embodiments, the composition of the invention is formulated for inhalation.

According to another embodiment, administration systemically is through an enteral route. According to another embodiment, administration through an enteral route is buccal administration. According to another embodiment, administration through an enteral route is oral administration. According to some embodiments, the composition is formulated for oral administration.

According to some embodiments, oral administration is in the form of hard or soft gelatin capsules, pills, capsules, tablets, including coated tablets, dragees, elixirs, suspensions, liquids, gels, slurries, syrups or inhalations and controlled release forms thereof.

Suitable carriers for oral administration are well known in the art. Compositions for oral use can be made using a solid excipient, optionally grinding the resulting mixture, and processing the mixture of granules, after adding suitable auxiliaries as desired, to obtain tablets or dragee cores. Non-limiting examples of suitable excipients include fillers such as sugars, including lactose, sucrose, mannitol, or sorbitol, cellulose preparations such as, maize starch, wheat starch, rice starch, potato starch, gelatin, gum tragacanth, methyl cellulose, hydroxypropylmethyl-cellulose, and sodium carbomethylcellulose, and/or physiologically acceptable polymers such as polyvinylpyrrolidone (PVP).

If desired, disintegrating agents, such as cross-linked polyvinyl pyrrolidone, agar, or alginic acid or a salt thereof, such as sodium alginate, may be added. Capsules and cartridges of, for example, gelatin for use in a dispenser may be formulated containing a powder mix of the composition of the invention and a suitable powder base, such as lactose or starch.

Solid dosage forms for oral administration include capsules, tablets, pill, powders, and granules. In such solid dosage forms, the composition of the invention is admixed with at least one inert pharmaceutically acceptable carrier such as sucrose, lactose, or starch. Such dosage forms can also comprise, as it normal practice, additional substances other than inert diluents, e.g., lubricating, agents such as magnesium stearate. In the case of capsules, tablets and pills, the dosage forms may also comprise buffering, agents. Tablets and pills can additionally be prepared with enteric coatings.

Liquid dosage forms for oral administration may further contain adjuvants, such as wetting agents, emulsifying and suspending agents, and sweetening, flavoring and perfuming agents. According to some embodiments, enteral coating of the composition is further used for oral or buccal administration. The term "enteral coating", as used herein, refers to a coating which controls the location of composition absorption within the digestive system. Non-limiting examples for materials used for enteral coating are fatty acids, waxes, plant fibers or plastics.

According to some embodiments, administering is administering topically. According to some embodiments, the composition is formulated for topical administration. The term "topical administration", as used herein, refers to administration to body surfaces. Non-limiting examples of formulations for topical use include cream, ointment, lotion, gel, foam, suspension, aqueous or cosolvent solutions, salve and sprayable liquid form. Other suitable topical product forms for the compositions of the present invention include, for example, emulsion, mousse, lotion, solution and serum.

According to another embodiment, the composition of the invention is administered to a subject in need thereof by a route selected from the group consisting of: intravenous, intraarterial, intramuscular, intralesional, transmucosal, subcutaneous, through inhalation and via direct injection into tissue or an organ. Each possibility represents a separate embodiment of the present invention. For certain applications, such as treatment of gastrointestinal disorders or diseases, enteral administration may be feasible.

In additional embodiments, the mitochondria composition of the present invention is administered through hair roots or hair follicles. Each possibility represents a separate embodiment of the present invention.

Most methods for mitochondrial transfer into cells require active transfer of the mitochondria by microinjection. Without wishing to be bound by any theory or mechanism, following administration of the mitochondria composition of the invention to a host cell, the mitochondria of the invention are transferred spontaneously into the host cell. Upon entering the host cell, the mitochondria of the invention may further merge (undergo fusion) with endogenous mitochondria within the host cell. Following fusion of the mitochondria of the invention with endogenous mitochondria within the host cell, the mitochondria may separate (undergo fission) which may increase ATP production in the cell, as is known in the art (Frazier A E, et al. Biol. Chem. 2006, 387(12):1551-8 and Parone et al. PLoS One. 2008, 22; 3(9):e3257).

According to some embodiments, the composition of the invention may further comprise agents such as, but not limited to: biotin, nicotinamide, betacarotene, coenzyme Q, selenium, superoxide dismutase, glutathione peroxide, uridine, creatine succinate, pyruvate, dihydroxyacetone, vitamin A, vitamin C, vitamin D, vitamin E, omega fatty acid, lithium carbonate, lithium citrate, calcium, vitamin K, folic acid, choline, vitamin $B_1$, vitamin $B_2$, vitamin $B_5$, vitamin $B_6$, vitamin $B_{12}$, acetyl-L-carnitine, alpha-lipoic acid, cardiolipin and a combination thereof. Each possibility represents a separate embodiment of the present invention.

According to another aspect, the present invention provides a pro-apoptotic protein delivery composition comprising a plurality of modified mitochondria comprising an intact mitochondrial outer membrane, the mitochondria harboring at least one exogenous pro-apoptotic protein.

According to another aspect, the present invention provides a method of pro-apoptotic protein delivery comprising:

providing a pharmaceutical composition comprising a plurality of modified mitochondria comprising an intact mitochondrial outer membrane, the mitochondria harboring at least one exogenous pro-apoptotic protein; and administering the composition comprising modified mitochondria to a subject in need thereof.

As used herein, the terms "modified mitochondria" and "modified mitochondria of the invention" are used interchangeably. As used herein, the term "modified mitochondria" refers to mitochondria harboring at least one pro-apoptotic protein. As used herein, the terms "harboring" and "comprising" are interchangeable. Typically, modified mitochondria refer to mitochondria isolated from a genetically modified source. As used herein, a genetic modified source refers to a cell harboring a foreign gene or foreign gene product. According to some embodiments, the modified mitochondria of the invention comprise an intact mitochondrial inner membrane. According to some embodiments, the modified mitochondria of the invention comprise an intact mitochondrial outer membrane. According to some embodiments, the modified mitochondria of the invention comprise intact mitochondrial inner and outer membrane. According to other embodiment, the modified mitochondria of the invention are functional.

As used herein, an "exogenous pro-apoptotic protein" refers to a pro-apoptotic protein which is not comprised in the un-modified mitochondria prior to modification. According to some embodiments, an "exogenous pro-apoptotic protein" refers to a pro-apoptotic protein which is comprised in the un-modified mitochondria prior to modification at a lower level than following modification.

According to some embodiments, an exogenous pro-apoptotic protein is a pro-apoptotic protein which is expressed in the cells from which the mitochondria are isolated or partially purified. Each possibility represents a separate embodiment of the present invention. Without wishing to be bound by any theory or mechanism, in some embodiments an exogenous pro-apoptotic protein which is expressed in cells may be delivered to the mitochondria of the cells, thus forming the modified mitochondria of the invention. According to some embodiments, the exogenous pro-apoptotic protein comprises a mitochondrial targeting sequence, targeting the pro-apoptotic protein to delivery to mitochondria. Without wishing to be bound by any theory or mechanism, combining more than one pro-apoptotic protein within the same modified mitochondria provides synergistic therapeutic effects.

As used herein, the term "pro-apoptotic protein" refers to a protein which may lead to apoptosis. As used herein, the terms "pro-apoptotic protein" and "biologically active agent" are used interchangeably. According to another embodiment, a pro-apoptotic protein induces cell death. According to another embodiment, the pro-apoptotic protein is a member of the Bcl-2 family. As used herein, the term "Bcl-2 family" refers to a family of proteins comprising a Bcl-2 homology (BH) domain. According to another embodiment, the pro-apoptotic protein is a pro-apoptotic member of the Bcl-2 family. According to another embodiment, the member of the Bcl-2 family is selected from the group consisting of: Bid, Bax, Puma, Bim, Bmf, Bad, Bcl-$X_S$, Erk, Bok and Bik. Each possibility represents a separate embodiment of the present invention. According to another embodiment, the pro-apoptotic protein is selected from the group consisting of: cytochrome c, apoptosis-inducing factor (AIF), a caspase and a procaspase. Included within the scope of pro-apoptotic proteins are pro-apoptotic proteins which are active per se, pro-apoptotic proteins that are activated upon contact with specific molecules in the body (e.g. activation by endogenous enzymes) and pro-apoptotic proteins that induce activity of other agents. Each possibility represents a separate embodiment of the present invention. Without wishing to be bound by any theory or mechanism, the modified mitochondria of the invention harboring a pro-apoptotic protein may be injected into a tumor to induce cell death of tumor cells.

The terms "polypeptide", "oligopeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

According to some embodiments, the modified mitochondria of the invention are prepared by transfecting the cells from which the mitochondria are derived with a nucleic acid encoding a desired gene or a desired gene and a sequence encoding a mitochondrial targeting sequence; and isolating or partially purifying the modified mitochondria. Each possibility represents a separate embodiment of the present invention. In a non-limiting example, transfecting DNA encoding a pro-apoptotic protein into a cell, results in expression of the encoded pro-apoptotic protein and its accumulation within the cell's mitochondria, thus resulting in modified mitochondria. According to another embodiment, the modified mitochondria of the invention are prepared by contacting isolated or partially purified mitochondria with a pro-apoptotic protein. According to some embodiments, the modified mitochondria of the invention are modified within the same cells from which they are derived. According to some embodiments, the modified mitochondria of the invention are modified within the same cells from which they are derived prior to the isolation or partial purification of the mitochondria. Each possibility represents a separate embodiment of the present invention.

According to some embodiments, the cells from which the modified mitochondria are derived are transfected with DNA comprising an expression cassette. An "expression cassette" refers to a natural or recombinantly produced polynucleotide that is capable of expressing a desired gene(s).

The term "recombinant" as used herein refers to a polynucleotide molecule that is comprised of segments of polynucleotides joined together by means of molecular biology techniques. The cassette contains the coding region of the gene of interest along with any other sequences that affect expression of the gene. A DNA expression cassette typically includes a promoter (allowing transcription initiation), and a sequence encoding one or more proteins. Optionally, the expression cassette may include, but is not limited to, transcriptional enhancers, non-coding sequences, splicing signals, transcription termination signals, and polyadenylation signals. An RNA expression cassette may include a translation initiation codon (allowing translation initiation) and a sequence encoding one or more proteins.

According to some embodiments, the pro-apoptotic protein comprises a targeting sequence which allows localization of the pro-apoptotic protein in a specific compartment within the mitochondria of the invention. According to another embodiment, the specific compartment within the mitochondria is selected from the group consisting of: mitochondrial outer membrane, mitochondrial inner membrane, mitochondrial matrix, mitochondrial inter-membrane space and a combination thereof. Each possibility represents a separate embodiment of the present invention. According to another embodiment, the pro-apoptotic protein is localized within a mitochondrial membrane. According to another embodiment, the pro-apoptotic protein is bound to a mitochondrial membrane. According to another embodiment, the pro-apoptotic protein binds the inner membrane, outer membrane or both membranes of the mitochondria.

Each possibility represents a separate embodiment of the present invention. According to another embodiment, the pro-apoptotic protein directly binds a mitochondrial membrane. According to another embodiment, the pro-apoptotic protein is linked to a mitochondrial membrane via a spacer. According to another embodiment, the pro-apoptotic protein is within the intermembrane space of the modified mitochondria. According to another embodiment, the pro-apoptotic protein is diffused within the matrix of the mitochondria. According to another embodiment, the pro-apoptotic protein is within the matrix of the mitochondria, bound to the inner membrane of the mitochondria directly or linked via a spacer. Each possibility represents a separate embodiment of the present invention.

As used herein, the term "a mitochondrial membrane" refers to a mitochondrial membrane selected from the group consisting of: the mitochondrial inner membrane, the mitochondrial outer membrane or a combination thereof.

As used herein the term "spacer" refers to a molecule linking between the pro-apoptotic protein and the modified mitochondria. In some embodiments the spacer is degradable to enable release of the biologically active agent at a target site.

In further embodiments the modified mitochondria of the invention are conjugated to cell targeting molecules enabling targeted pro-apoptotic protein delivery. The cell targeting molecules may be selected from the group consisting of: antibodies, oligosaccharides, peptides and carbohydrates. Each possibility represents a separate embodiment of the present invention.

The following examples are presented to provide a more complete understanding of the invention. The specific techniques, conditions, materials, proportions and reported data set forth to illustrate the principles of the invention are exemplary and should not be construed as limiting the scope of the invention.

EXAMPLES

Example 1

Mitochondrial Transfer into 3T3-L1 Cells and Fusion with Endogenous Mitochondria In order to detect mitochondrial entrance to cells and fusion with endogenous mitochondria, the split Luciferase-YFP assay was employed using fibroblast 3T3-L1 cells. Cells were transfected with a construct encoding the C-terminal portion of *Renilla luciferase*, the C-terminal portion of YFP and a mitochondrial targeting sequence (termed C-Luc-YFP) and selected for stably expressing cells using Neomycin. Similarly, a 3T3-L1 cell line stably expressing the N-Luc-YFP construct had been prepared (N-Luc-YFP encoding the N-terminal portion of *Renilla luciferase*, the N-terminal portion of YFP and a mitochondrial targeting sequence). Mitochondria were extracted from 3T3-L1 cells expressing the N-Luc-YFP construct, using the following protocol:
1. Cells were trypsininzed and washed 3 times in 1 ml of buffer M1 (100 mM sucrose, 20 mM Tris-MOPS, 1 mM EGTA).
2. Cells were Incubated on ice in 1 ml buffer M2 (100 mM sucrose, 20 mM Tris-MOPS, 1 mM EGTA, 5% Percoll) for 5 minutes.
3. Cells were centrifuged at a speed of 2500 g for 5 minutes at 4° C. Supernatant was transferred to a polypropylene tube and kept on ice.
4. The pellet was washed in 1 ml buffer M2 and re-centrifuged at a speed of 2500 g for 5 minutes at 4° C.
5. The supernatant was added to the supernatant of step 3 and centrifuged at a speed of 12,000 g for 12 minutes at 4° C. Supernatant was discarded.
6. The pellet containing mitochondria was re-suspended in 100 µl of buffer M3 (250 mM sucrose, 20 mM Tris-MOPS, 1 mM EGTA).

Figure 1B:
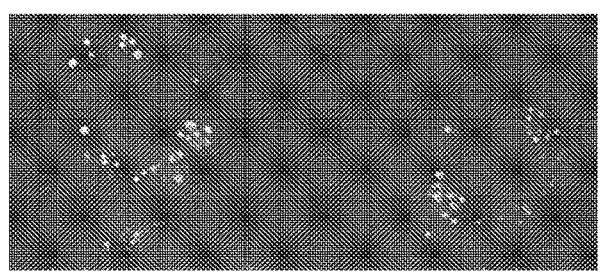
FIG. 1B is a micrograph showing YFP complementation in 3T3-L1 cells expressing C-Luc-YFP and treated with mitochondria extracted from cells expressing N-Luc-YFP.

Cells expressing C-Luc-YFP were either left untreated, or incubated with the mitochondria extracted from the N-Luc-YFP expressing cells for 150 or 240 minutes. The *Renilla* luciferase detection kit (Promega) was used to assay the luciferase expression. FIG. 1A depicts luciferase expression as percentage of the luciferase expression in the untreated cells after 150 minutes. As can be seen in FIG. 1A, the luciferase level was higher in cells that were treated with mitochondria, indicating that the mitochondria entered the cells and fused with the endogenous mitochondria, thus allowing the complementation of a functional luciferase protein. To further verify mitochondrial fusion, cells were treated with mitochondria for 24 hours, seeded in 24-wells plates, underwent fixation and observed using a Zeiss microscope. FIG. 1B shows the YFP staining that was detected, indicating that the exogenous and endogenous mitochondria have fused, allowing the complementation a functional YFP protein.

Example 2

Figure 2:
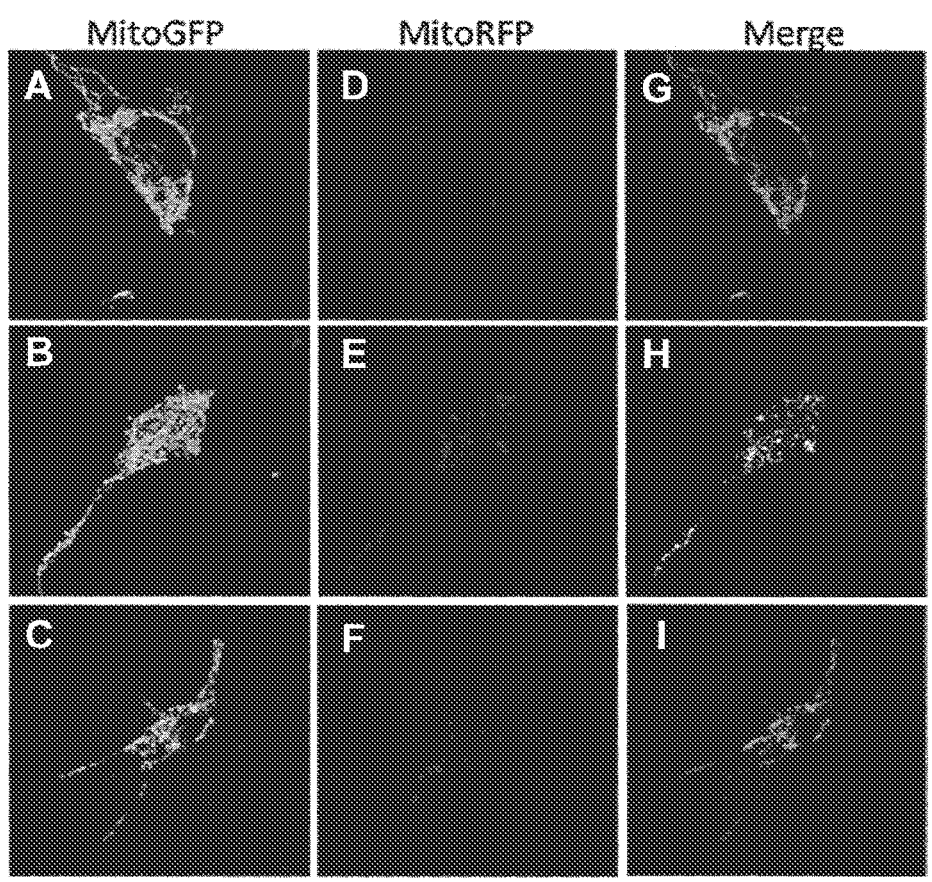
FIG. 2 is a micrograph showing labeled mitochondria isolated from MitoRFP expressing cells and incubated with MitoGFP expressing cells. Cells were imaged using a confocal microscope equipped with a x63 magnification oil immersion lens.

Exogenous Mitochondria Transfer and Co-localization with Endogenous Mitochondria in 3T3-L1 Cells 3T3-L1 cells were labeled with mitochondrial GFP (Mito-GFP) or RFP (MitoRFP) and 24 hours later mitochondria were isolated from the MitoRFP expressing cells and incubated with the MitoGFP expressing cells. The cells were fixed and viewed under a Leica confocal microscope (FIG. 2).

All the merged cells showed both green and red staining, indicating red labeled mitochondria entered MitoGFP expressing cells (merge column). Some of the cells showed dispersion of red labeled exogenous mitochondria throughout the cells (FIGS. 2D and 2E), as compared to the green staining of the endogenous mitochondria (FIGS. 2A and 2B, respectively). This resulted in co-localization of both colors (FIGS. 2G and 2H), suggesting the mitochondria in the fusion-fission processes are functional.

Some of the cells showed more punctate staining of the exogenous labeled mitochondria (FIG. 2F). Co-localization was less pronounced in these cells (FIG. 2I).

Example 3

Placental Mitochondria Incubated with 3T3-L1 Cells Increase Citrate Synthase Activity and ATP Production Mitochondria were isolated from mouse term placenta, bovine placenta or human placentas according to the following protocol:
1. Placenta was rinsed free of blood by using ice-cold IB (isolation buffer: 200 mM sucrose, 1 mM EGTA and 10 mM Tris-MOPS)+0.2% BSA.
2. The placenta was minced into small pieces in 5 ml IB+0.2% BSA using scissors.

3. The suspension was transferred to a (10 ml) glass potter and homogenized using a Dounce glass homogenizer by five complete up and down cycles.
4. The homogenate was transferred to a 15 ml tube and centrifuged at 600 g for 10 min at 4° C.
5. The supernatant was transferred to clean centrifuge tubes and the pellet was resuspended in IB+0.2% BSA, and subjected to a second centrifugation step.
6. The supernatant was recovered and centrifuged at 7,000×g for 15 min.
7. The supernatant was discarded and the pellet was resuspended in 10 ml ice-cold IB and centrifuged at 600 g for 10 min at 4° C.
8. The mitochondria were recovered from the supernatant by centrifuging at 7,000×g for 15 min at 4° C.
9. The supernatant was discarded and the pellet resuspended, containing mitochondria in 200 µl of IB.
10. Protein content was determined by the Bradford assay.

Figure 3A:
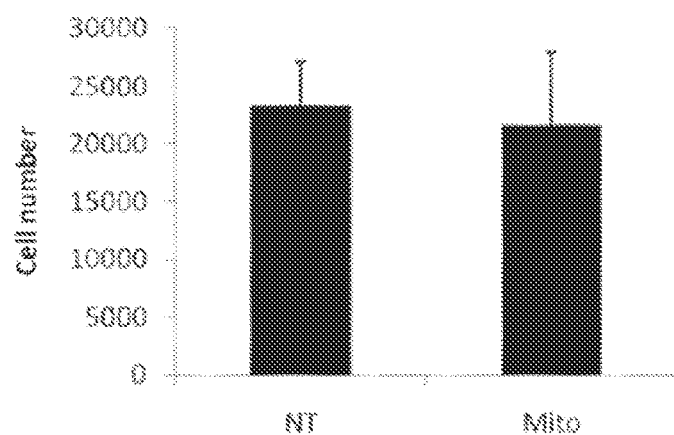
FIGS. 3A-3C are bar graphs showing a comparison of cell number (FIG. 3A), ATP contents (FIG. 3B) and citrate synthase activity (FIG. 3C) between 3T3-L1 cells enriched with bovine placental mitochondria (Mito) and control cells (NT).
Figure 3B:
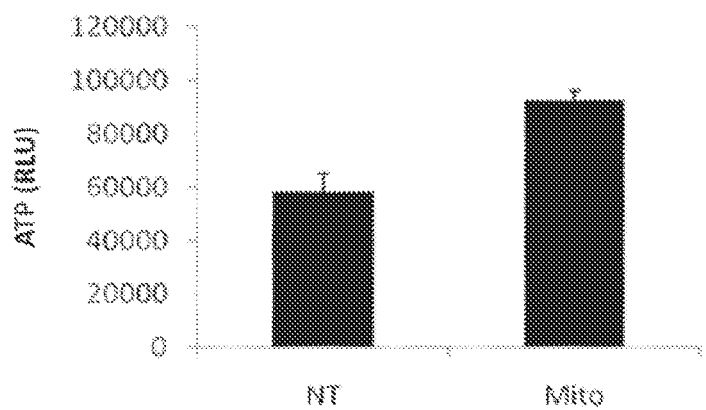
Figure 3C:
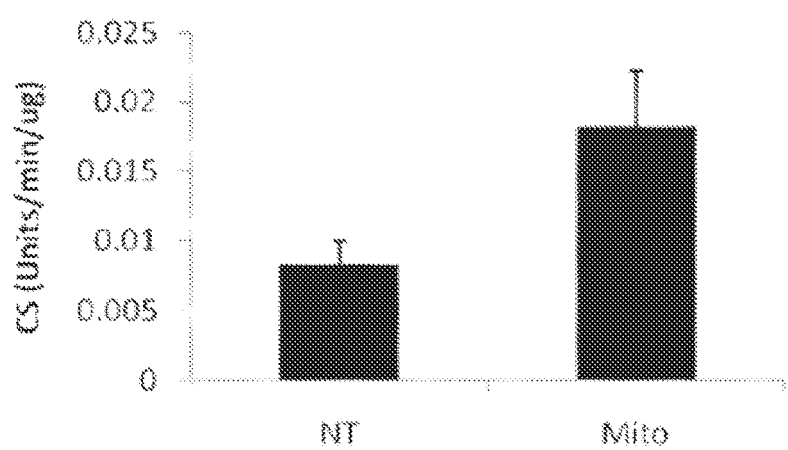

3T3-L1 cells were cultured in 24 wells plates until confluent and subsequently incubated with 20 µg of mitochondria in 200 µl of growing media (DMEM+10% Bovine serum) for 24 hours. The cells were washed in PBS, trypsinized and transferred to 4 wells of 24 wells plate. Twenty four hours later the cells were washed in PBS and trypsinized. 3T3-L1 cells, which were not incubated with the mitochondria preparation described above, were used as control cells (not treated, NT). As depicted in FIG. 3A, no significant difference was observed between the number of cells grown comprising the exogenous mitochondria (Mito) and control cells (NT). However, ATP content, measured using ATPlight by Perkin-Elmer, was significantly increased in the Mito cells as compared to control (FIG. 3B). In addition, the level of citrate synthase activity, measured using the citrate synthase assay kit by Sigma, was significantly increased in the Mito cells as compared to control cells (FIG. 3C), suggesting an increase in mitochondria number and function.

Example 4

Increased ATP Activity in Endothelial Cells Enriched with CGP37157-Treated Mitochondria Mitochondria were isolated from 400 mg mouse term placenta according to the protocol described in Example 3. At step 2, the placenta was minced in the presence or absence of 80 µM CGP37157 (Sigma®), a mitochondrial $Na^+/Ca^{+2}$ exchanger blocker.

Figure 4:
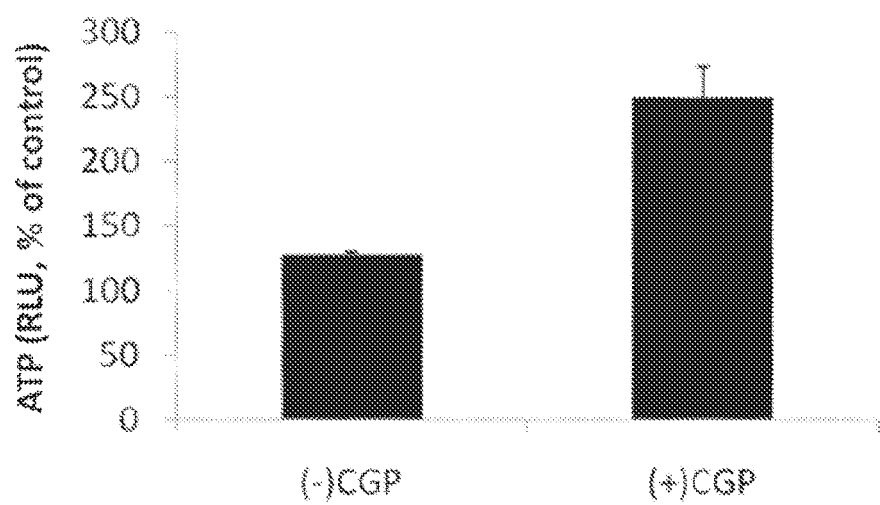
FIG. 4 is a bar graph showing ATP level in bEND3 cells cultured with mitochondria in the presence or absence of CGP37157.

Brain mouse endothelial cells (bEND3) were cultured in 24 wells plates until confluent. Cells were left untreated or incubated with 18 µg of the above described mitochondria preparation in 200 µl of DMEM+10% fetal bovine serum for 24 hours. As a control, cells were incubated with a mitochondria preparation which was not treated with CGP37157. Cells were then washed in PBS, trypsinized and cultured for an additional 24 hours. As shown in FIG. 4, the ATP level was significantly increased in cells comprising exogenous mitochondria which were pretreated with CGP37157 ((+) CGP) in the isolation process, as compared to control cells ((−) CGP). The data in FIG. 4 is presented as percentage relative to the non-treated cells.

Example 5

Rescue of 143B Rho0 mtDNA Depleted Cells by Transfer of Exogenous Mitochondria

The 143B Rho0 cells are devoid of mtDNA and thus cannot support normal oxidative phosphorylation and must survive and replicate using ATP derived solely from glycolysis. Consequently, 143B Rho0 cells can only replicate if supplied with pyruvate and uridine. In order to examine whether transfer of exogenous mitochondria can rescue mtDNA depleted cells, 143B Rho0 cells were seeded in 96 well plates (30,000 cells/well) and cultured in a medium containing pyruvate and uridine.

Figure 5A:
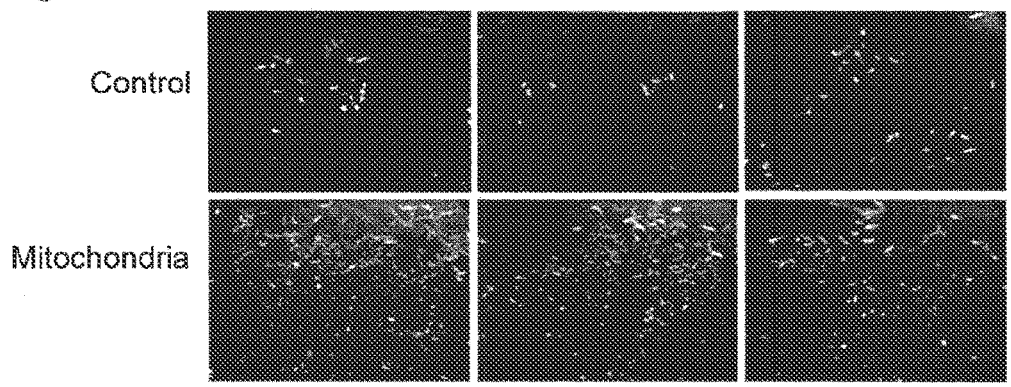
FIG. 5A is a micrograph showing 143B Rho0 cells with or without pre-incubation with mitochondria derived from 143B TK cells.
Figure 5B:
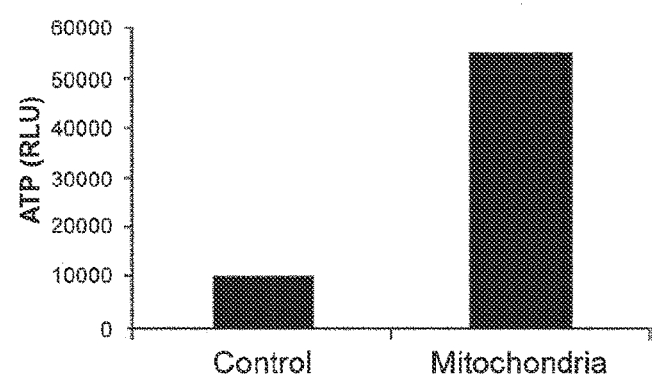
FIGS. 5B-5C are bar graphs depicting ATP production of 143B Rho0 cells with or without pre-incubation with mitochondria derived from 143B TK cells (FIG. 5B) or with human placental mitochondria treated or non-treated with CGP (FIG. 5C).

Mitochondria were isolated from 143B TK cells ($2*10^6$ cells per well; 5A, 5B) or from human placenta with or without 80 µM of CGP37157 ($Na^+/Ca^{2+}$ ion-exchanger inhibitor; 5C). The mitochondria were incubated with the 143B Rho0 cells for 24 hours, after which the medium was replaced and the cells were treated with Ganciclovir to exclude 143B TK cells that might have survived the isolation procedure (5A, 5B). After 3 days, the cell medium was replaced to a medium which is pyruvate and uridine-free. After 24 hours the cells were trypsinized and transferred to 10 cm dishes. The medium was replaced every 3 days for the next 9 days, after which cells were photographed using a Zeiss microscope (FIG. 5A) and ATP level was determined in 100 µl of trypsinized cells using the ViaLight kit (Lonza) (FIGS. 5B,C).

Figure 5C:
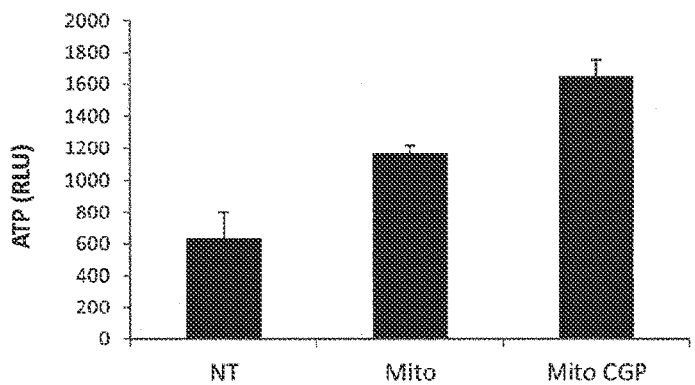

As can be seen (FIG. 5A), cells containing exogenous mitochondria showed a much higher proliferation than control cells. The ability of single cells to create big colonies of cells suggests that the exogenous mitochondria are transferred to daughter cells and remain active. Furthermore, cells containing exogenous mitochondria from 134B TK cells (FIG. 5B) or human placenta cells (FIG. 5C) displayed higher ATP production than control cells. Cells containing exogenous mitochondria from human placenta and CGP37157 show higher ATP production than cells treated with human placenta mitochondria without CGP37157 (FIG. 5C).

Example 6

Figure 6:
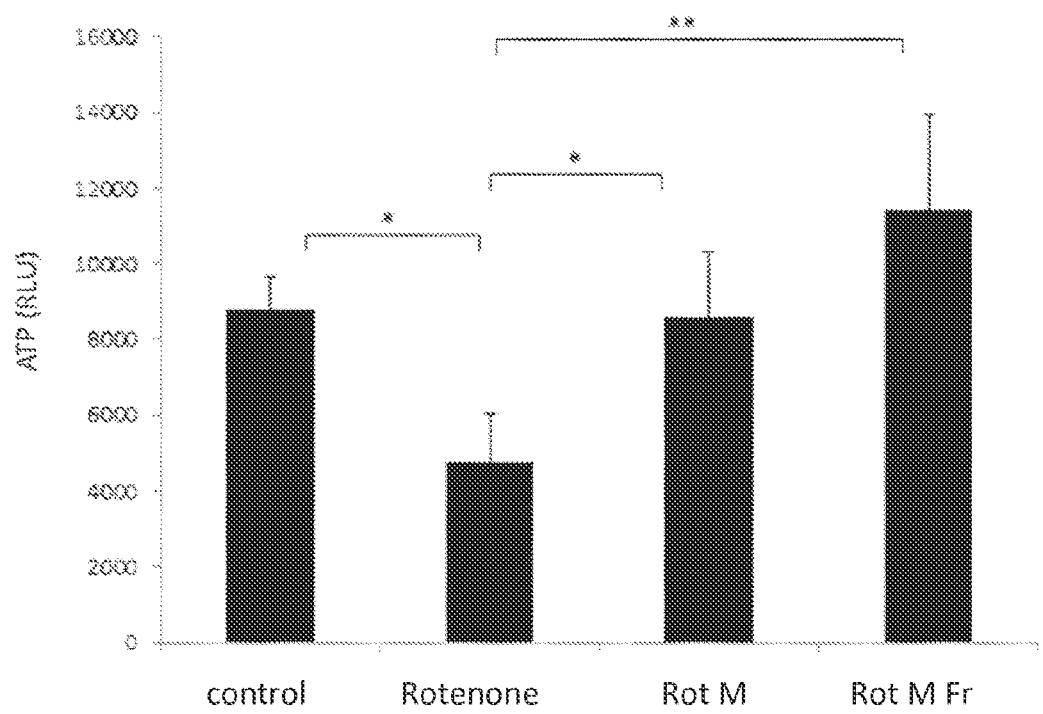
FIG. 6 is a bar graph depicting ATP production in mouse 3T3-L1 cells that were either untreated (control), treated with the mitochondrial complex I inhibitor Rotenone (Rotenone), treated with Rotenone and mitochondria (Rot M) or treated by Rotenone and mitochondria that were frozen for 5 days at −20° C. and thawed (Rot M Fr).

Fresh Isolated Mitochondria or Mitochondria that were Frozen and Thawed can Rescue ATP Production of Rotenone-induced Mitochondrial Inhibition Mouse 3T3-L1 cells (30,000 cells) were either untreated (Control) or incubated with the mitochondrial complex I inhibitor Rotenone (0.5 µM) for 4 hours. Following incubation cells were washed and either left untreated (Rotenone), treated with 2 µg of fresh mouse placental mitochondria (Rot M) or treated with 2 µg of mouse placental mitochondria that were frozen and thawed (Rot M Fr) in 50 µl IB. Mitochondria activity was assayed by measuring ATP production using the ViaLight kit (Lonza). As can be seen in FIG. 6, cells that were treated with frozen mitochondria show rescue of Rotenone-inhibited ATP production at least to the same extent as cells that were treated with fresh mitochondria, suggesting that frozen mitochondria are at least as effective as fresh mitochondria.

Example 7

Mitochondria that were Frozen and Thawed Show Higher Oxygen Consumption

Mitochondria were isolated from human term placenta according to the following protocol:
1. Placenta was rinsed free of blood by using ice-cold IB buffer (isolation buffer: 200 mM sucrose, 1 mM EGTA and 10 mM Tris-MOPS)+0.2% BSA.

2. The placenta was minced into small pieces in 5 ml IB+0.2% BSA using scissors.
3. The suspension was transferred to a 10 ml glass potter and homogenized using a Dounce glass homogenizer by five complete up and down cycles.
4. The homogenate was transferred to a 15 ml tube and centrifuged at 600 g for 10 min at 4° C.
5. The supernatant was transferred to clean centrifuge tubes and the pellet was resuspended in IB buffer, and subjected to a second centrifugation step.
6. The supernatant from steps 4 and 5 was filtered through a 5 μm filter to remove any cells or large cell debris.
7. The supernatant was recovered and centrifuged at 7,000×g for 15 min.
8. The mitochondrial pellet was washed in 10 ml ice cold IB buffer and mitochondria were recovered by centrifugation at 7,000×g for 15 min at 4° C.
9. The supernatant was discarded and the pellet resuspended, containing mitochondria in 200 μl of IB buffer.
10. Protein content was determined by the Bradford assay.

Figure 7:
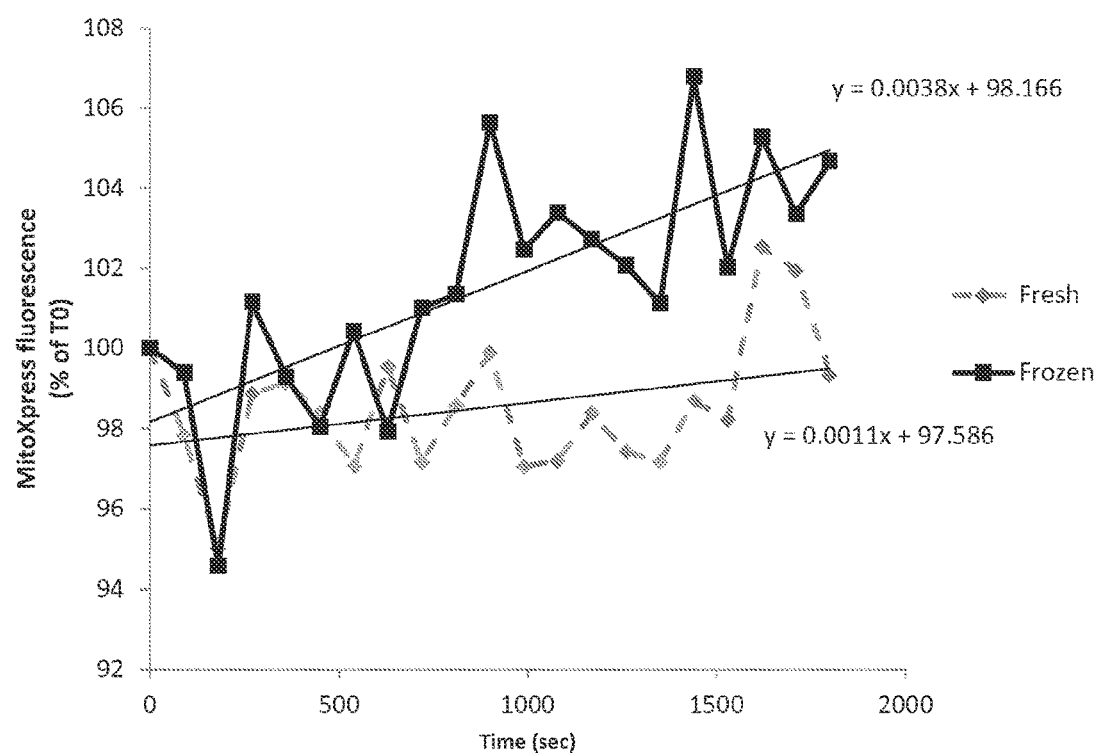
FIG. 7 is a dot-plot showing $O_2$ consumption in frozen vs. fresh mitochondria over time.

To compare activity of frozen versus unfrozen mitochondria, mitochondria were flash-frozen in IB (200 mM sucrose, 1 mM EGTA and 10 mM Tris-MOPS) in 1.5 ml Eppendorf tubes and kept at −70° C. for 30 minutes. Mitochondria were thawed quickly by hand and $O_2$ consumption by 20 μg mitochondria was measured using the MitoXpress fluorescence probe (Luxcel) and a Tecan plate reader. The percentage change in fluorescence was calculated relative to the level of fluorescence at time 0. A trendline was plotted to determine the average change in fluorescence over time which stands for the rate of $O_2$ consumption (the slope of the line). FIG. 7 shows that the $O_2$ consumption, and rate of $O_2$ consumption, were higher for mitochondria that were frozen and thawed (marked "Frozen") in comparison to non-frozen mitochondria (marked "Fresh").

As opposed to frozen mitochondria, mouse placental mitochondria that were chilled (kept for 4 days at 4° C.) produced less ATP than fresh mitochondria (Table 1). Moreover, when 60,000 bEND3 endothelial cells were treated for 24 hours with 18 mg of mitochondria in 24 well plates, it could be seen that chilled mitochondria reduced ATP production and induced caspase activity (Table 2).

TABLE 1

ATP production of fresh and chilled mouse placental mitochondria

|  | ATP (RLU) |
|---|---|
| Fresh Mitochondria (F) | 4690 |
| Chilled Mitochondria (C) | 1587 |

TABLE 2

ATP production and caspase induction in cells treated with fresh or chilled mitochondria

|  | ATP | Caspases |
|---|---|---|
| Non-Treated Cells | 173387 | 0.16 |
| Cells treated with fresh mitochondria | 226967 | 0.13 |
| Cells treated with chilled mitochondria | 86074 | 0.22 |

Example 8

Mitochondria Suspended in a Buffer Containing a High Sucrose Concentration Show Higher Oxygen Consumption Placental human mitochondria were prepared as described in Example 7 and suspended in isolation buffer (200 mM sucrose, 1 mM EGTA, 10 mM Tris-MOPS; M). Mitoplasts (mitochondria lacking the outer membrane; according to Murthy and Pande, 1987) were prepared by using 10 times diluted IB (20 mM sucrose, 0.1 mM EGTA, 1 mM Tris-MOPS) on the last isolation step (MP). Oxygen consumption over time was measured for 25 μg of mitochondria or mitoplasts using the MitoXpress fluorescence probe (Luxcel) and a Tecan plate reader. The percentage of change in fluorescence was calculated relative to the level of fluorescence at time 0. A trendline was plotted to determine the average change in fluorescence over time which stands for the rate of $O_2$ consumption (the slope of the line).

Figure 8:
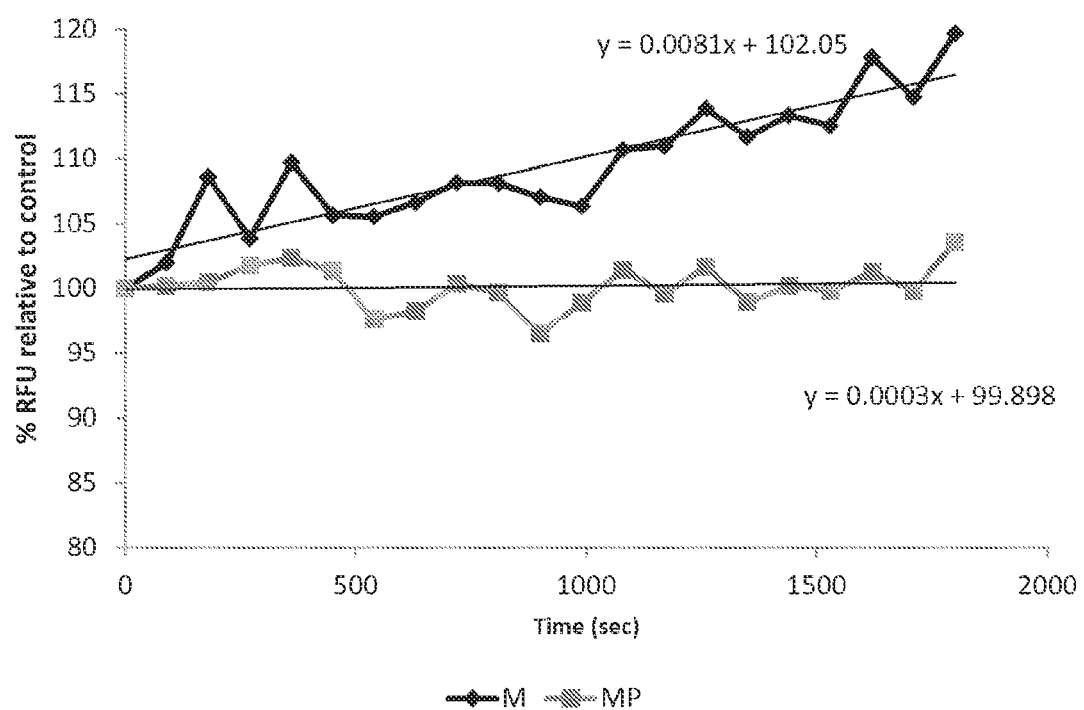
FIG. 8 is a dot-plot showing $O_2$ consumption over time in a mitochondria composition comprising 20 mM sucrose (MP) or 200 mM sucrose (M).

As can be seen in FIG. 8, the rate of oxygen consumption was higher in mitochondria that were suspended in a buffer containing 200 mM sucrose.

Example 9

Figure 9A:
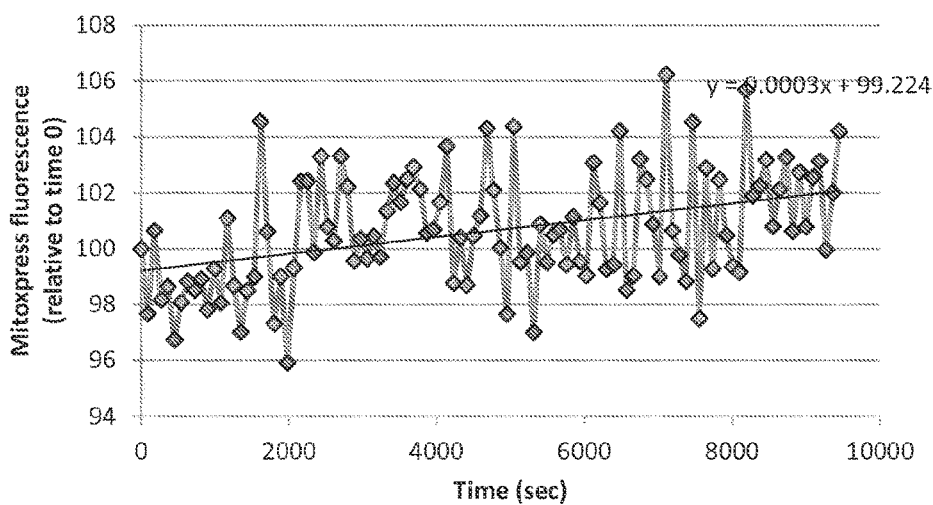
FIGS. 9A-9B are dot plots, depicting $O_2$ consumption over time in mitochondria that were frozen in a buffer comprising sucrose (FIG. 9A, IB buffer) or a buffer comprising trehalose (FIG. 9B, AT buffer).
Figure 9B:
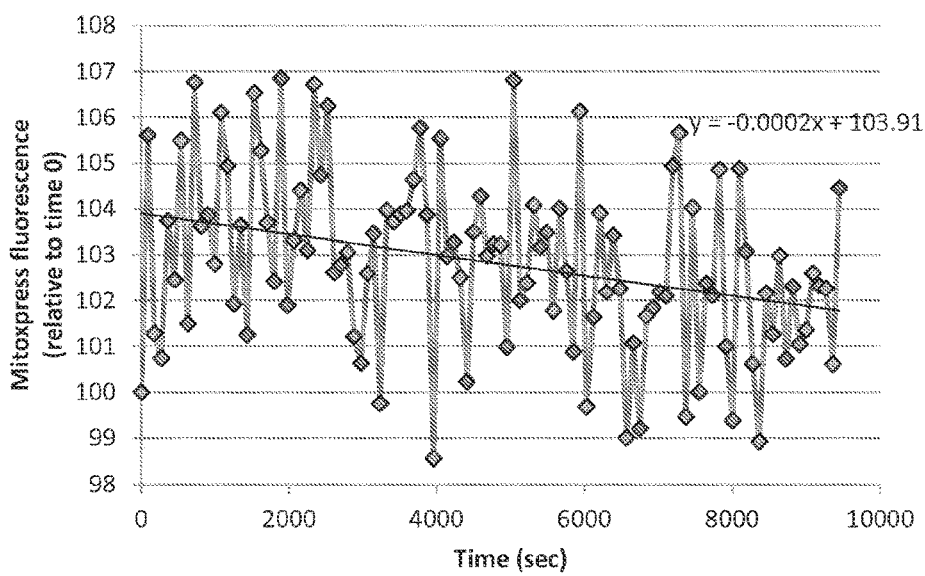

Oxygen Consumption of Mitochondria that have been Frozen and Thawed in Different Buffers Mouse placental mitochondria were isolated essentially as described in Example 7. The mitochondria were suspended either in Isolation buffer (IB) containing 200 mM sucrose, 1 mM EGTA, 10 mM Tris-MOPS (Frezza et al., Nature Protocols, 2007, (2)2:287-295) or, in a comparative example, in AT buffer (AT) containing 300 mM trehalose, 10 mM HEPES-KOH pH=7.7, 10 mM KCl, 1 mM EGTA, 1 mM EDTA and 0.1% BSA (Yamaguchi et al., Cell Death and Differentiation, 2007, (14):616-624). Mitochondria were frozen immediately after isolation at −80° C. for 24 hours, thawed quickly by hand and assayed for oxygen consumption using the MitoXpress kit, correlating oxygen consumption with fluorescence. The change in fluorescence was plotted over time and linear trendlines were extrapolated. A positive slope was observed for the mitochondria isolated and frozen in IB (FIG. 9A), suggesting active mitochondria, while a negative slope was observed for mitochondria isolated and frozen in AT buffer (FIG. 9B), suggesting inactive mitochondria. Taken together, the results suggest that isolating and freezing mitochondria in IB containing high sucrose (200 mM) maintains superior mitochondrial activity.

Example 10

Cell Proliferation of Human Fibroblasts with or without Incubation with Mitochondria that have been Frozen for a Month Prior to Use Human placental mitochondria were isolated in Isolation buffer (See IB in example 7) and immediately frozen at −80° C. One month following freezing, the mitochondria were quickly thawed and 2 μg were used to treat human skin fibroblast cells derived from patients suffering from a mitochondrial disorder. Cells were grown in a glucose containing buffer (UP buffer—permissive medium containing DMEM, 4.5 g/L glucose, 10% fetal calf serum, 50 μg/ml uridine and 110 μg/ml pyruvate) and incubated with the mitochondria for 24 hours. Following incubation with the mitochondria, cells were incubated in a glucose deprived medium (GAL buffer—restrictive glucose-free DMEM medium supplemented with 10% dialyzed fetal calf serum and 5 mM galactose) for additional 48 hours. Cell proliferation was measured by staining cells with Methylene Blue (staining cell nuclei).

Figure 10:
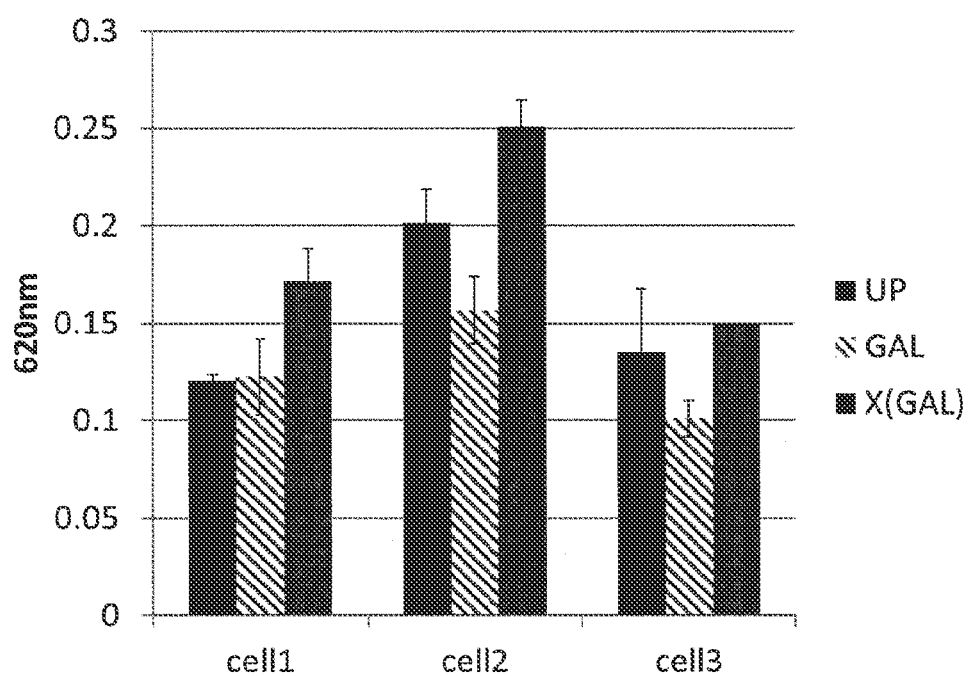
FIG. 10 is a bar graph, showing proliferation of human fibroblasts derived from patients suffering from a mitochondrial disorder, with or without incubation with mitochondria that have been frozen for a month prior to use.

FIG. 10 shows comparison of cell proliferation between 3 cell types:

UP—cells which were not incubated with mitochondria and were grown in a permissive buffer.

GAL—cells which were not incubated with mitochondria, grown in a permissive buffer for 24 hours and in a restrictive buffer for 48 hours.

X(GAL)—cells which were incubated with mitochondria, grown in a permissive buffer for 24 hours and in a restrictive buffer for 48 hours.

As can be seen in FIG. 10, cell proliferation was improved in cells that were incubated with mitochondria as compared to cells that were not incubated with mitochondria. Cells derived from 3 patients were used in this experiment (termed cell 1, 2, 3, respectively)—cell 1 represents cells from patients having a genomic TMRU mitochondrial mutation, cell 2 represents cells from patients having a SUCLA mitochondrial mutation and cell 3 represents control fibroblasts.

Example 11

Transfer of Exogenous Mitoplasts Fails to Rescue ATP Production in 143B Rho0 mtDNA Depleted Cells In order to produce mitoplasts, mitochondria were isolated from 400 mg human term placenta in 10 ml isolation buffer (IB) containing 200 mM sucrose, 1 mM EGTA, 10 mM Tris-MOPS+0.2% BSA, incubated for 10 minutes in ice-cold IB diluted 1:10 in double distilled water (DDW) and centrifuged at a speed of 10,000 g for 15 minutes. Mitochondria were isolated as described in Example 7. Next, 2 μg of the mitochondria (M) or mitoplasts (MP) were incubated with 30,000 143B Rho0 cells in a 96-well plate. Following 24 hours of incubation the medium was replaced and cells were grown for additional 72 hours in complete growth medium (containing pyruvate and uridine). The medium was replaced with a growth medium devoid of pyruvate and uridine, the cells were grown for additional 5 days and ATP level was measured using the ViaLight kit (Lonza).

Figure 11:
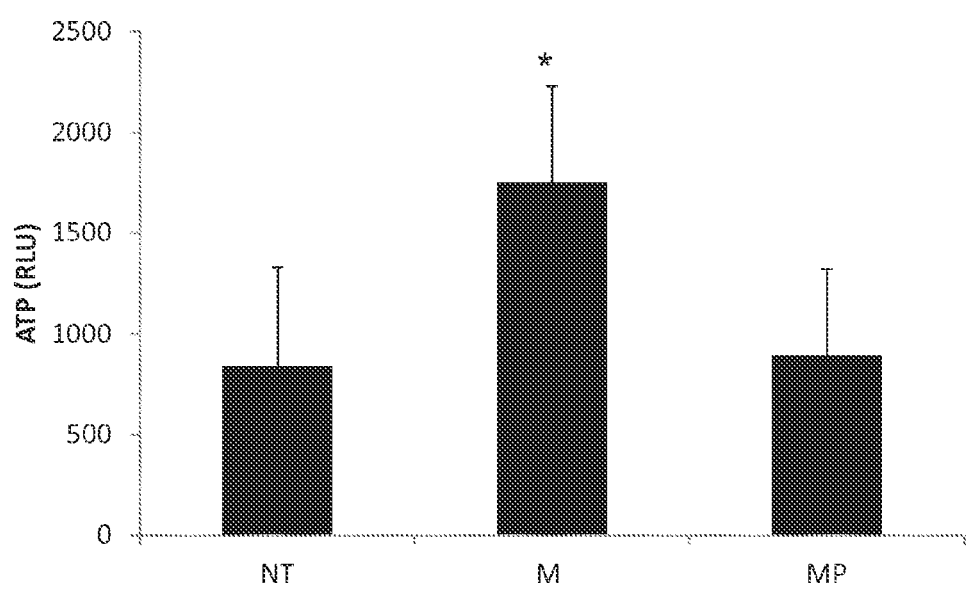
FIG. 11 is a bar graph showing ATP level in 143B Rho0 cells and 143B Rho0 cells that were incubated with mitoplasts or mitochondria.

As can be seen in FIG. 11, incubation with mitoplasts failed to induce an increase in ATP levels in the 143B Rho0 cells, as opposed to incubation with mitochondria.

Example 12

Progesterone Synthesis in Human Isolated Mitochondria is Decreased Following Treatment with Protease Inhibitors Mitochondria were isolated from 400 mg human term placenta in 10 ml isolation buffer (IB) containing 200 mM sucrose, 1 mM EGTA, 10 mM Tris-MOPS+0.2% BSA in the presence or absence of a protease inhibitor cocktail (Sigma P8340, X100). Next, 20 μg of the mitochondria were incubated in 200 μl of Bovine Serum (Biological Industries, Israel) and progesterone levels within the serum were measured using a radioimmunoassay at the beginning of incubation (T0) and following a 24 hours incubation at 37° C. and 5% $CO_2$.

Figure 12A:
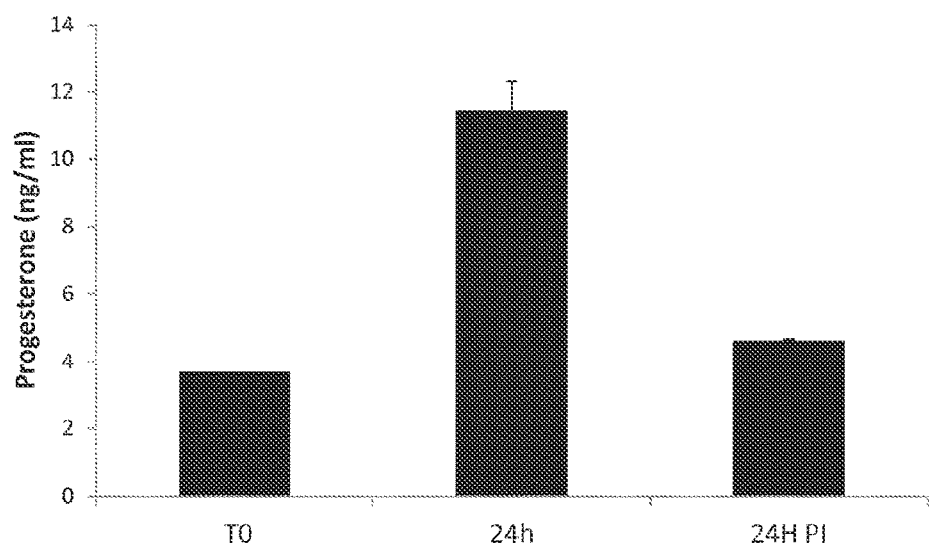
FIGS. 12A-12B are bar graphs showing progesterone production in mitochondria and mitochondria that were contacted with a protease inhibitor cocktail (FIG. 12A) and in mitochondria that were frozen for 5 days (FIG. 12B).

As can be seen in FIG. 12A, use of protease inhibitors resulted in reduced progesterone synthesis by the human placental mitochondria.

Figure 12B:
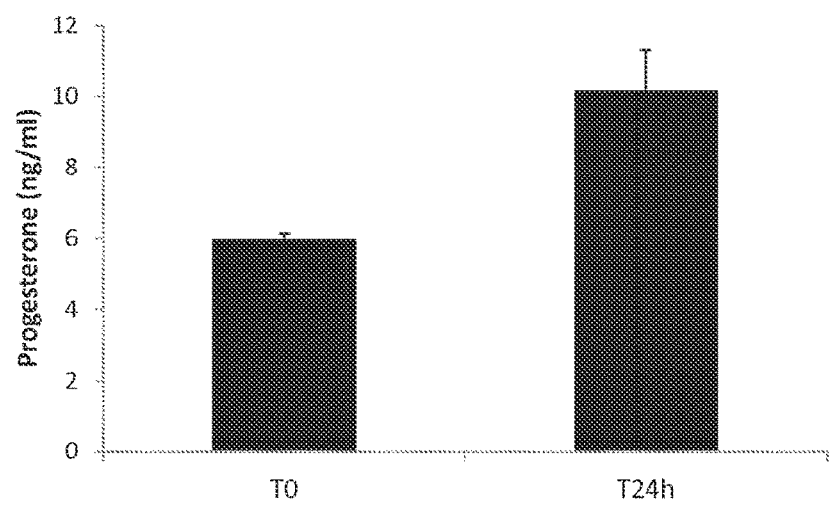

The level of progesterone was also measured in mitochondria that were frozen for 5 days at −80° C., thawed and incubated for 24 h in bovine serum. As can be seen in FIG. 12B, human placental mitochondria that were frozen and thawed after 5 days retain their ability to produce progesterone.

Example 13

Figure 13:
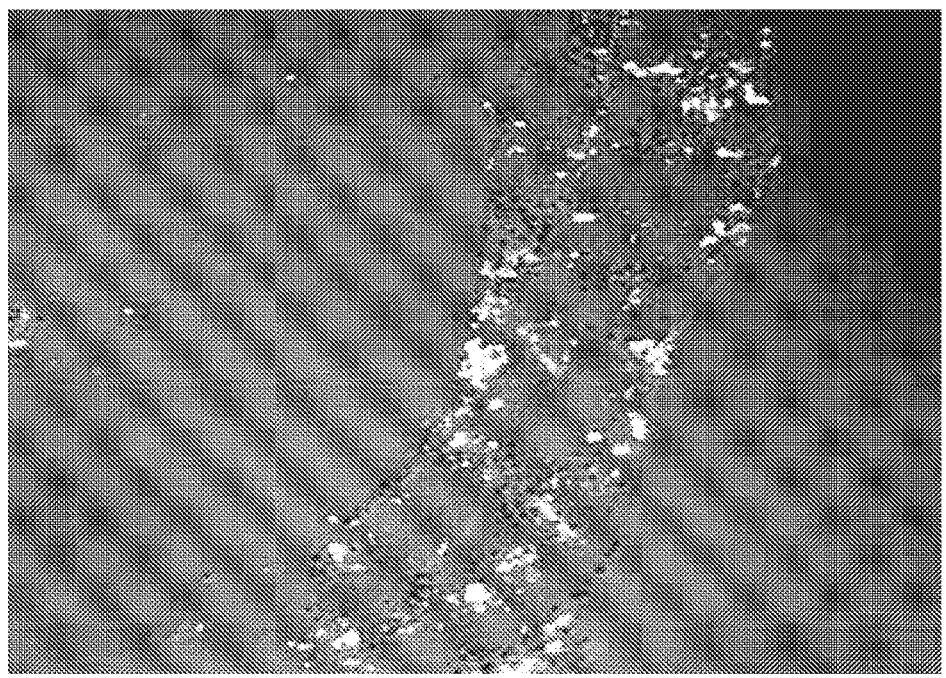
FIG. 13 is a micrograph showing human CYP11A1 immunostaining of 143B Rho0 cells that were treated with human placental mitochondria.

Human Placental Mitochondria Incubated with Non-steroidogenic 143B Rho0 Cells Enabled Steroidogenic Activity Mitochondria were isolated from human placenta and incubated (5 μg) with 60,000 143B Rho0 cells which were seeded on coverslips in wells of a 24-well plate. After 24 hours of incubation within a medium containing pyruvate and uridine the medium was replaced and the cells were incubated for additional 48 h hours. Cells were fixed using 2.5% PFA and immunostained for human CYP11A1 (a mitochondrial enzyme which catalyzes the first reaction in the process of steroidogenesis). No staining was seen in control cells, but as can be seen in FIG. 13, punctate staining was observed in cells treated with the mitochondria.

Example 14

Human Placental Mitochondria Incubated with Non-steroidogenic 3T3-L1 Cells Increase Progesterone Synthesis Mitochondria were isolated from human term placenta, according to the protocol described in Example 7.

3T3-L1 cells were cultured in 24-well plates until confluent and subsequently incubated with 18 or 36 μg of mitochondria in 200 μl of growing media (DMEM+10% bovine serum) for 24 hours.

The medium was collected first after 24 hours and progesterone level was determined by RadioImmunoAssay (RIA). The cells incubated with 36 μg of mitochondria were then washed in PBS, trypsinized and transferred to 4 wells of a 24 well plate with fresh growing medium and grown for an additional 48 hours. The medium was collected for the second time and progesterone level was determined. Both 3T3-L1 cells which were not incubated with the isolated mitochondria and isolated mitochondria incubated in growing medium without cells were used as controls (incubated for 24 hours). As depicted in Table 3, at 24 hours, incubation of 3T3-L1 cells with elevated amounts of mitochondria, namely 18 μg and 36 μg, resulted in an increase in progesterone production from 0.26 ng/ml to 0.83 ng/ml respectively, while no progesterone was detected in the two control samples. 3T3-L1 cells incubated for 48 h, beginning after the first collection at 24 hours and in fresh medium, showed no progesterone synthesis.

TABLE 3

| Level of progesterone synthesis | | | |
|---|---|---|---|
| Sample | Mitochondria content | Time | Progesterone (ng/ml) |
| 3T3-L1 cells | — | 24 hours | Not detected* |
| Medium of 3T3-L1 cells | 18 µg | 24 hours | 0.26 |
| Medium of 3T3-L1 cells | 36 µg | 24 hours | 0.83 |
| Medium of 3T3-L1 cells | 36 µg | 48 hours (starting from 24 h) | Not detected* |
| Medium | 36 µg | 24 hours | Not detected* |

Example 15

Isolation of Human Placental Mitochondria Using IB Results In Higher ATP and Progesterone Production Human placental mitochondria were isolated from 650 mg placental pieces, and isolated either by using IB (as in Example 7) or using the method described by Pinkert et al. (Pinkert et al. Transgenic Res. 1997, 6(6):379-83). The levels of citrate synthase (CS) and ATP were measured in 18 µg of mitochondria. The progesterone level in the medium of non-steroidogenic 3T3-L1 cells incubated with 36 µg of mitochondria was further analyzed using a radioimmunoassay (RIA). As can be seen in Table 4, the amount of mitochondria (as measured by citrate synthase levels) indicates that both isolation methods resulted in a similar amount of mitochondria. However, ATP and progesterone levels were lower in mitochondria isolated by Pinkert's method.

TABLE 4

| Comparison of mitochondria isolation methods | | | |
|---|---|---|---|
| | ATP (RLU) | CS (u/min/mg) | Progesterone (pg/ml) |
| Pinkert | 256 | 2.4 | 0.4 |
| IB | 2257 | 2.24 | 0.83 |

The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention.

The invention claimed is:

1. A pharmaceutical composition comprising:
a plurality of partially purified functional human mitochondria that have undergone a freeze-thaw cycle, the plurality of partially purified functional human mitochondria having an oxygen consumption rate comparable to or higher than that of control mitochondria that have not undergone a freeze-thaw cycle, the partially purified functional human mitochondria having an intact outer membrane; and
sucrose in an amount sufficient to preserve mitochondrial function,
wherein the total amount of mitochondrial proteins is between 20%-80% of the total amount of cellular proteins within said composition, and
wherein the composition is devoid of exogenous protease inhibitors.

2. The pharmaceutical composition of claim 1, wherein said partially purified functional mitochondria are derived from a cell or a tissue selected from the group consisting of placenta, placental cells grown in culture and blood cells.

3. The pharmaceutical composition of claim 1, further comprising a buffer, the buffer being the same type of buffer as an isolation buffer used to isolate said partially purified functional mitochondria.

4. The pharmaceutical composition of claim 1, wherein said partially purified functional mitochondria are reduced in size by exposure to an ion-exchanger inhibitor.

5. The pharmaceutical composition of claim 1, wherein said freeze-thaw cycle comprises freezing said partially purified functional mitochondria for at least 24 hours prior to thawing.

6. The pharmaceutical composition of claim 1, wherein the total amount of mitochondrial proteins is between 20%-50% of the total amount of cellular proteins within said composition.

7. The pharmaceutical composition of claim 1, wherein said freeze-thaw cycle comprises freezing said partially purified functional mitochondria within a freezing buffer, said freezing buffer comprising a saccharide.

8. The pharmaceutical composition of claim 7, wherein said saccharide is sucrose.

9. A pharmaceutical composition comprising:
a plurality of isolated functional human mitochondria that have undergone a freeze-thaw cycle, the plurality of isolated functional human mitochondria having an oxygen consumption rate comparable to or higher than that of control mitochondria that have not undergone a freeze-thaw cycle, the isolated functional human mitochondria having an intact outer membrane, and
sucrose in an amount sufficient to preserve mitochondrial function,
wherein the weight of the mitochondria constitutes more than 80% of the combined weight of the mitochondria and other sub-cellular fractions, and wherein the composition is devoid of exogenous protease inhibitors.

* * * * *